(12) United States Patent
Beckett et al.

(10) Patent No.: US 6,358,987 B1
(45) Date of Patent: Mar. 19, 2002

(54) METALLOPROTEINASE INHIBITORS

(75) Inventors: Raymond Paul Beckett; Fionna Mitchell Martin; Andrew Miller; Richard Simon Todd; Mark Whittaker, all of Oxford (GB)

(73) Assignee: British Biotech Pharmaceuticals Limited, Oxford (GB)

( * ) Notice: Subject to any disclaimer, the term of this patent is extended or adjusted under 35 U.S.C. 154(b) by 0 days.

(21) Appl. No.: 09/798,162

(22) Filed: Mar. 5, 2001

Related U.S. Application Data

(62) Division of application No. 09/462,632, filed on Jan. 11, 2000, now Pat. No. 6,271,262.

(30) Foreign Application Priority Data

Jul. 18, 1997 (GB) ................................................ 9715030

(51) Int. Cl.$^7$ ................... A61K 31/4164; C07D 233/58
(52) U.S. Cl. ................... 514/400; 548/336.1; 546/340; 514/357
(58) Field of Search ................... 514/400, 357; 548/336.1; 546/340

(56) References Cited

FOREIGN PATENT DOCUMENTS

| EP | 0 497 192 A | 8/1992 |
|----|-------------|--------|
| WO | 96 23791 A  | 8/1996 |
| WO | 97 47599 A  | 12/1997 |

*Primary Examiner*—Charanjit S. Aulakh

(74) *Attorney, Agent, or Firm*—Banner & Witcoff, Ltd.

(57) ABSTRACT

A compound of formula (I)

wherein
X is —COOH or —CONHOH
Y is a group of formula (ID) or (IE)

(ID)

(IE)

or a pharmaceutically acceptable salt, hydrate, or solvate thereof. The compounds are inhibitors of matrix metalloproteinases involved in tissue degradation.

32 Claims, No Drawings

METALLOPROTEINASE INHIBITORS

This application is a divisional of Ser. No. 09/462,632, filed Jan. 11, 2000, now U.S. Pat. No. 6,271,262.

The present invention relates to therapeutically active hydroxamic and carboxylic acid derivatives, to processes for their preparation, to pharmaceutical compositions containing them, and to the use of such compounds in medicine. In particular, the compounds are inhibitors of matrix metalloproteinases involved in tissue degradation.

BACKGROUND TO THE INVENTION

The matrix metalloproteinases (MMPs) are a family of enzymes including interstitial collagenase, neutrophil collagenase, collagenase-3, 72 kDa gelatinase, 92 kDa gelatinase, stromelysin-1, stromelysin-2, stromelysin-3, matrilysin, macrophage metalloelastase, membrane-type metalloproteinase-1 and membrane-type metalloproteinase-2. These enzymes share a common zinc-containing catalytic domain and a pro-sequence which maintains latency. A wide range of cells and tissues can express MMPs in response to activation by inflammatory stimuli such as interleukin-1 or tumour necrosis factor-α (TNF-α). Different stimuli can induce overlapping yet distinct repertoires of MMPs and different cell types can respond to the same stimuli by expression of distinct combinations of MMPs. MMPs can attack the protein components of extracellular matrix such as collagens, vitronectin and elastin, and have recently been shown to process membrane proteins such as pro-TNF-α to release soluble TNF-α. MMPs are thought to play a central role in the pathology of inflammatory diseases such as rheumatoid arthritis as well as in the growth and metastasis of tumours.

Compounds which have the property of inhibiting the action of MMPs are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas.

Two known classes of pseudopeptide or peptide mimetic MMP inhibitors have a hydroxamic acid group or a carboxylic group respectively as their zinc binding groups. Many such known MMPs may be represented by the structural formula (IA)

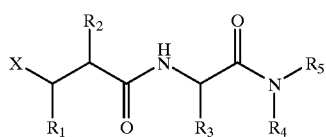

(IA)

in which X is the zinc binding hydroxamic acid (—CONHOH) or carboxylic acid (—COOH) group and the groups $R_1$ to $R_5$ are variable in accordance with the specific prior art disclosures of such compounds.

The following patent publications disclose such MMP inhibitors:

| US 4599361 | (Searle) | WO 95/04033 | (Celltech) |
|---|---|---|---|
| EP-A-2321081 | (ICI) | WO 95/04735 | (Syntex) |
| EP-A-0236872 | (Roche) | WO 95/04715 | (Kanebo) |
| EP-A-0274453 | (Bellon) | WO 95/06031 | (Immunex) |
| WO 90/05716 | (British Biotech) | WO 95/09841 | (British Biotech) |
| WO 90/05719 | (British Biotech) | WO 95/12603 | (Syntex) |
| WO 91/02716 | (British Biotech) | WO 95/19956 | (British Biotech) |
| WO 92/09563 | (Glycomed) | WO 95/19957 | (British Biotech) |
| US 5183900 | (Glycomed) | WO 95/19961 | (British Biotech) |
| US 5270326 | (Glycomed) | WO 95/19965 | (Glycomed) |
| WO 92/17460 | (SB) | WO 95/22966 | (Sanofi Winthrop) |
| EP-A-0489577 | (Celltech) | WO 95/23790 | (SB) |
| EP-A-0489579 | (Celltech) | WO 95/32944 | (British Biotech) |
| EP-A-0497192 | (Roche) | WO 95/33709 | (Roche) |
| US 5256657 | (Sterling) | WO 96/06074 | (British Biotech) |
| WO 92/13831 | (British Biotech) | WO 96/16027 | (Syntex/Agouron) |
| WO 92/22523 | (Research Corp) | WO 96/16931 | (British Biotech) |
| WO 93/09090 | (Yamanouchi) | WO 96/23791 | (Syntex) |
| WO 93/09097 | (Sankyo) | WO 96/29313 | (Procter & Gamble) |
| WO 93/20047 | (British Biotech) | WO 96/33161 | (British Biotech) |
| WO 93/24449 | (Celltech) | WO 96/33165 | (British Biotech) |
| WO 93/24475 | (Celltech) | WO 96/33166 | (DuPont Merck) |
| EP-A-0574758 | (Roche) | WO 96/33968 | (Fuji YKKK) |
| EP-A-0575844 | (Roche) | WO 96/33991 | (Sankyo) |
| WO 94/02446 | (British Biotech) | WO 97/02239 | (British Biotech) |
| WO 94/02447 | (British Biotech) | WO 97/03966 | (British Biotech) |
| WO 94/21612 | (Otsuka) | WO 97115553 | (Sankyo) |
| WO 94/21625 | (British Biotech) | WO 97/19053 | (British Biotech) |
| WO 94/24140 | (British Biotech) | | |
| WO 94/25434 | (Celltech) | | |
| WO 94/25435 | (Celltech | | |

M. A. Abreo et al. presented a poster entitled "Truncated Succinamide Hydroxamates With Nanomolar Potency against various MMPS" at the 213th ACS Meeting in San Francisco, Apr. 13th–17th 1997. In that poster compounds of formula (IC) were disclosed:

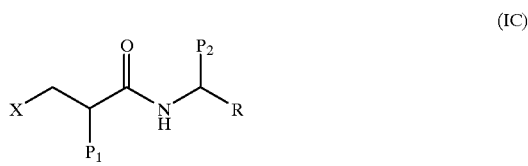

(IC)

wherein X is —COOH or —CONHOH, $P_1$ is biphenylpropyl, R is hydroxymethyl and $P_2$ is the side chain found in one of the following amino acids, namely serine, tert-butylglycine, histidine, O-benzylthreonine, phenylalanine, tyrosine, methionine, threonine, and 3-(3-pyridyl)alanine. Also disclosed were compounds of formula (IC) wherein X and $P_1$ are as just defined, and P2 and R together with the carbon atom to which they are attached form a trans-cyclohexan-2-ol or glucosyl ring. The authors stated that the compound (IC), $P_2$=the histidine side chain and R=hydroxymethyl, showed good plasma levels after iv and oral dosing to mice. They also stated that the X-ray crystal structure of compound (IC), $P_2$=tert-butyl and R=hydroxymethyl, was obtained with stromelysin-1, and that the hydroxyl moiety in R makes an H-bond in the $P_3$ area of the enzyme, while the tert-butyl group makes good hydrophobic contact in the $P_2$ area.

BRIEF DESCRIPTION OF THE INVENTION

This invention makes available a novel class of compounds which are inhibitors of matrix metalloproteinases. The compounds of the invention conform to general formula (IA), or have structural features similar to those of Abreo et. al., but differ in structure from prior art compounds of formula (IA) or (IC) principally in the identity of the group $R_1$. In the compounds of the present invention, the group $R_1$ is a sulfonamidoalkyl group.

DETAILED DESCRIPTION OF THE INVENTION

According to the present invention there is provided a compound of formula (I)

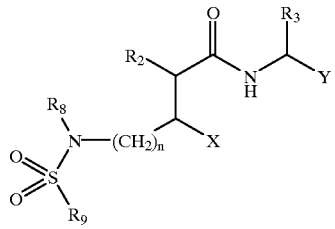

(I)

wherein

X is —COOH or —CONHOH n is 1, 2, 3 or 4;

$R_2$ is a
- $C_1$–$C_{12}$ alkyl,
- $C_2$–$C_{12}$ alkenyl,
- $C_2$–$C_{12}$ alkynyl,
- phenyl($C_1$–$C_6$ alkyl)-,
- heteroaryl($C_1$–$C_6$ alkyl)-,
- non-aryl heterocyclyl($C_1$–$C_6$ alkyl)-,
- cycloalkyl($C_1$–$C_6$ alkyl)-,
- cycloalkenyl($C_1$–$C_6$ alkyl)-,
- phenoxy($C_1$–$C_6$ alkyl)-,
- heteroaryloxy($C_1$–$C_6$ alkyl)-,
- phenyl($C_1$–$C_6$ alkyl)O($C_1$–$C_6$ alkyl)-,
- heteroaryl($C_1$–$C_6$ alkyl)O($C_1$–$C_6$ alkyl)-,
- phenyl($C_1$–$C_6$ alkyl)S($C_1$–$C_6$ alkyl)- or
- heteroaryl($C_1$–$C_6$ alkyl)S($C_1$–$C_6$ alkyl)- group, any one of which may be optionally substituted by $C_1$–$C_6$ alkyl, trifluoromethyl, $C_1$–$C_6$ alkoxy, halo, cyano (—CN), phenyl, substituted phenyl or heteroaryl; or $R_3$ represents the characterising group of a natural or non-natural α amino acid in which any functional groups may be protected;

$R_8$ is hydrogen, $C_1$–$C_6$ alkyl, benzyl, acyl, optionally substituted phenyl, optionally substituted heterocyclyl, an amino protecting group, or a group —$(CH_2)_m$COZ where m is an integer from 1 to 6, and Z represents OH, $C_1$–$C_6$ alkoxy or —$NR_xR_y$ where $R_x$, $R_y$ each independently represent hydrogen or $C_1$–$C_6$ alkyl; and $R_9$ is optionally substituted $C_1$–$C_6$ alkyl, cycloalkyl, cycloalkenyl, di-($C_1$–$C_6$ alkyl)amino, heterocyclyl, phenyl, naphthyl, or heteroaryl; or $R_8$ and $R_9$ taken together represent a divalent $C_3$–$C_6$ alkylene or alkenylene group which may optionally be (i) substituted by an oxo group, and/or (ii) substituted by ($C_1$–$C_6$)alkoxy, hydroxy, mercapto, ($C_1$–$C_6$) alkylthio, amino, halo (including fluoro, chloro, bromo and iodo), cyano, trifluoromethyl, nitro, —COOH, —$CONH_2$, —$CONHR^A$ or —$CONR^AR^A$ wherein $R^A$ is a ($C_1$–$C_6$)alkyl group, and/or (iii) fused to a phenyl or heteroaryl group which itself may be substituted;

Y Is a group of formula (ID) or (IE)

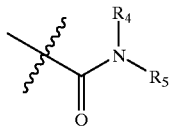

(ID)

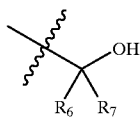

(IE)

wherein:

$R_4$ represents
(a) an optionally substituted cycloalkyl or cycloalkenyl ring; or
(b) a phenyl or heteroaryl ring which may be fused to a benzene or heteroaryl ring, either or both of which rings may be substituted, and in which any ring nitrogen atom may be oxidised as an N-oxide, or
(c) a group —$CHR^xR^y$ wherein $R^x$ and $R^y$ each independently represents an optionally substituted phenyl or heteroaryl ring which may be linked covalently to each other by a bond or by a $C_1$–$C_4$ alkylene or $C_2$–$C_4$ alkenylene bridge;
(d) a group of formula —$(Z'—O)_w$—Z wherein Z' is straight or branched $C_1$–$C_8$ alkyl optionally interrupted by one or more non-adjacent S and/or N atoms, w is an integer >1, and no continuous linear sequence of atoms in the group $R_4$ is >12, or
(e) a straight or branched $C_1$–$C_6$ alkyl group, optionally interrupted by one or more non-adjacent S and/or N atoms, which is substituted by at least two substituents of formula —$(Z''')_x$—$(OZ)_q$ wherein Z''' is straight or branched $C_1$–$C_6$ alkyl optionally interrupted by one or more non-adjacent S and/or N atoms, x is 0 or 1, q is 1 or 2, and no continuous linear sequence of atoms in the group $R_4$ is >12, or
(f) hydrogen, $C_1$–$C_6$ alkyl, $C_1$–$C_4$ perfluoroalkyl, or a group D-($C_1$–$C_6$ alkyl)- wherein D is hydroxy, $C_1$–$C_6$ alkoxy, $C_1$–$C_6$ alkylthio, acylamino, optionally substituted phenyl or heteroaryl, $NH_2$, or mono- or di-($C_1$–$C_6$ alkyl)amino or N-morpholino;

or $R_3$ and $R_4$ taken together represent a divalent chain of formula —$C(R^a)(R^b)$—A''—Alk— wherein $R^a$ and $R^b$ are independently hydrogen or $C_1$–$C_6$ alkyl, A'' is a bond, —O—, —S—, —S—S—, —NH— or —$NR^a$— wherein $R^a$ is $C_1$–$C_6$ alkyl, and Alk is $C_1$–$C_6$ alkylene;

$R_5$ is hydrogen or a $C_1$–$C_6$ alkyl group;

$R_6$ is hydrogen, $C_1$–$C_6$ alkyl, phenyl($C_1$–$C_6$ alkyl), heterocyclyl($C_1$–$C_6$ alkyl), optionally substituted phenyl, or optionally substituted heterocyclyl;

$R_7$ is is hydrogen or a $C_1$–$C_6$ alkyl group;

or (when $R_7$ is hydrogen) $R_3$ and $R_7$ taken together with the carbon atoms to which they are attached form a 2-hydroxycyclohexyl or $C_6$ sugar (hexose) ring;

or $R_6$ and $R_7$ taken together with the carbon atom to which they are attached form a 5 or 6-membered carbocyclic or heterocyclic ring;

and pharmaceutically acceptable salts, hydrates and solvates thereof.

As used herein the term "alkyl" means a straight or branched chain alkyl moiety. The term "($C_x$–$C_y$)alkyl"

where x and y are integers means an alkyl group having having from x to y carbon atoms. The term "lower alkyl" means an alkyl group having having from 1 to 6 carbon atoms.

The term "alkenyl" means a straight or branched chain alkenyl moiety having at least one double bond of either E or Z stereochemistry where applicable. The term "$(C_x–C_y)$ alkenyl" where x and y are integers means an alkenyl group having having from x to y carbon atoms. The term "lower alkenyl" means an alkenyl group having from 1 to 6 carbon atoms.

The term "alkynyl" means a straight or branched chain alkynyl moiety having at least one triple bond. The term "$(C_x–C_y)$alkynyl" where x and y are integers means an alkynyl group having having from x to y carbon atoms. The term "lower alkynyl" means an alkynyl group having having from 1 to 6 carbon atoms.

The term "cycloalkyl" means a saturated alicyclic ring having from 3–8 carbon atoms and includes, for example, cyclopropyl, cyclobutyl, cyclopentyl, cyclohexyl, cycloheptyl and cyclooctyl.

The term "cycloalkenyl" as used herein means an unsaturated alicyclic ring having from 5–8 carbon atoms, incorporating at least one double bond, and includes, for example, cyclopentenyl, cyclohexenyl, cycloheptenyl and cyclooctenyl.

The term "acyl" as used herein means a group RC(=O)— wherein R is $C_1–C_6$ alkyl or substituted $C_1–C_6$ alkyl, phenyl or substituted phenyl, phenyl($C_1–C_6$ alkyl)- or subtituted phenyl($C_1–C_6$ alkyl)-.

The term "non-aryl heterocyclyl" means a 5–7 membered heterocyclic ring containing one, two or three heteroatoms selected from S, N and O in which at least two adjoining atoms are saturated. Examples include morpholinyl, thiomorpholinyl, dihydrofuranyl, tetrahydrothienyl, dihydrothienyl, piperidinyl, pyrrolidinyl, pyrrolinyl, dioxolanyl, oxathiolanyl, imidazolinyl, imidazolidinyl, pyrazolinyl, pyrazolidinyl, pyranyl, dioxanyl, dithianyl, oxathianyl, and piperazinyl.

The term "heteroaryl" means a 5–7 membered aromatic heterocyclic ring containing one or more heteroatoms selected from S, N and O and optionally fused to a benzene ring. Illustrative of such rings are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with up to four substituents, each of which independently may be $(C_1–C_6)$alkoxy, hydroxy, mercapto, $(C_1–C_6)$alkylthio, amino, halo (including fluoro, chloro, bromo and iodo), cyano, trifluoromethyl, nitro, —COOH, —CONH$_2$, —CONHR$^A$ or —CONR$^A$R$^A$ wherein R$_A$ is a $(C_1–C_6)$alkyl group or the residue of a natural alpha-amino acid, or substituted with a phenyl or heteroaryl group which itself may be substituted by any of the foregoing.

The term "side chain of a natural or non-natural alpha-amino acid" means the group R in a natural or non-natural amino acid of formula NH$_2$—CH(R)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, a-aminoadipic acid, a-amino-n-butyric acid, 3,4-dihydroxyphenylalanine, homoserine, a-methylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When R$_3$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1–C_6$ alkyl ester), amino groups may be converted to amides (for example as a NHCOC$_1$— $C_6$ alkyl amide) or carbamates (for example as an NHC (=O)OC$_1$—C$_6$ alkyl or NHC(=O)OCH$_2$Ph carbamate), hydroxyl groups may be converted to ethers (for example an OC$_1$—C$_6$ alkyl or a O(C$_1$–C$_6$ alkyl)phenyl ether) or esters (for example a OC(=O)C$_1$–C$_6$ alkyl ester) and thiol groups may be converted to thioethers (for example a tert-butyl or benzyl thioether) or thioesters (for example a SC(=O) C$_1$–C$_6$ alkyl thioester).

Examples of side chains of non-natural alpha amino acids include those referred to below in the discussion of suitable R$_3$ groups for use in compounds of the present invention.

Salts of the compounds of the invention include physiologically acceptable acid addition salts for example hydrochlorides, hydrobromides, sulfates, methane sulfonates, p-toluenesulfonates, phosphates, acetates, citrates, succinates, lactates, tartrates, fumarates and maleates. Salts may also be formed with bases, for example sodium, potassium, magnesium, and calcium salts.

There are at least two chiral centres in the compounds according to the invention because of the presence of asymmetric carbon atoms. The presence of these asymmetric carbon atoms gives rise to a number of diastereomers with R or S stereochemistry at each chiral centre. General formula (1), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the X group—S,

C atom carrying the R$_2$ group—R,

C atom carrying the R$_3$ group—S, but mixtures in which the above configurations predominate are also contemplated.

As mentioned above, the compounds of the present invention differ in structure from the collagenase inhibitors disclosed in the patent publications listed above principally in that they have the above defined R$_9$—(SO$_2$)—N(R$_8$)— (CH$_2$)$_n$— group on the carbon atom carrying the hydroxamic acid group. Accordingly the groups R$_2$, R$_3$, R$_4$, R$_5$, R$_6$ and R$_7$ of the compounds of this invention may include those which have been disclosed in the corresponding positions of compounds disclosed in any of the patent publications listed above.

Without limiting the generality of the foregoing, examples of substituents R$_2$ to R$_9$ are given below:

The Group R$_2$

In the compounds of the invention, two classes of substituent R$_2$ are those having formula (A) or (B):

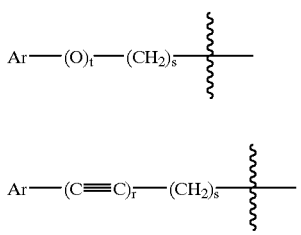

(A)

(B)

wherein

| Ar | represents an optionally substituted phenyl or heteroaryl group; |
|---|---|
| r | is 1 or 2; |
| s | is 0, 1, 2, 3 or 4; and |
| t | is 0 or 1. |

In this type of $R_2$ group:
(i) heteroaryl Ar groups may be bonded via a ring carbon atom in Ar or (in the case where t is 0) via a ring nitrogen atom in Ar;
(ii) when the group Ar is substituted, preferably only one substituent is present. In 6 membered Ar groups, such as phenyl and pyridyl, the substituent is preferably in the 4-position of the ring relative to the bond connecting Ar to the rest of group (II). In 5 membered Ar groups, such as thienyl and furanyl, the substituent is preferably in the 3- or 4-position of the ring relative to the bond connecting Ar to the rest of group (II);
(iii) a sole substituent in Ar may be selected from $C_1$–$C_6$ alkyl eg methyl, ethyl, n-propyl, n-butyl, n-pentyl and n-hexyl; $C_1$–$C_6$ alkoxy($C_1$–$C_6$ alkoxy), 2-methoxyethoxy, trifluoromethyl, halo eg chloro, cyano (—CN), —CH$_2$CN, —OH, or —OR, wherein R is $C_1$–$C_6$ alkyl or benzyl;
(iv) another sole substituent in Ar may be a phenyl, phenoxy, phenylthio, heteroaryl (eg 2-, 3- or 4-pyridyl), heteroaryloxy (eg 2-, 3- or 4pyridyloxy) or heteroarylthio ((eg 2-, 3- or 4-pyridylthio) group which is either unsubstitued or substituted with one substituent selected from $C_1$–$C_6$ alkyl eg methyl, ethyl, n-propyl, n-butyl, n-pentyl and n-hexyl; $C_1$–$C_6$ alkoxy($C_1$–$C_6$ alkoxy), 2-methoxyethoxy, trifluoromethyl, halo eg chloro, cyano (—CN), —CH$_2$CN, —OH, and —OR, wherein R is $C_1$–$C_6$ alkyl or benzyl;
(v) r may be 1 or 2 and s may be 1.

The $R_2$ group present in the compounds of the invention may be:
optionally substituted $C_1$–$C_{12}$ alkyl, $C_3$–$C_6$ alkenyl, $C_3$–$C_6$ alkynyl, or cycloalkyl($C_1$–$C_6$ alkyl); or
phenyl($C_1$–$C_6$ alkyl)- or phenoxy($C_1$–$C_6$ alkyl)-, either of which may be optionally substituted in the phenyl ring by halogen, cyano, $C_1$–$C_6$ alkyl, or $C_1$–$C_6$ alkoxy; or
biphenyl($C_1$–$C_6$ alkyl)-, 4'-phenoxy(phenyl($C_1$–$C_6$ alkyl))-, 4'-pyrid-2,3 or 4-yl(phenyl($C_1$–$C_6$ alkyl))-, or 4'-pyrid-2,3 or 4-yloxy(phenyl($C_1$–$C_6$ alkyl))-, any of which may optionally be substituted in the terminal phenyl or pyridyl ring by halogen, cyano, $C_1$–$C_6$ alkyl, or $C_1$–$C_6$ alkoxy.

Specific examples of $R_2$ groups present in the compounds of the invention include isopropyl, iso-butyl, n-pentyl, n-hexyl, n-heptyl, n-octyl, n-nonyl, n-decyl, cyclopropylmethyl, cyclobutylmethyl, cyclopentylmethyl, cyclohexylmethyl, 1,1,1-trifluoropropyl, phenylpropyl, 4-chlorophenylpropyl, 4-methylphenylpropyl, 4-methoxyphenylpropyl, 4-phenyl-phenylpropyl, 4-(4-chlorophenyl)phenylpropyl, 4-phenoxyphenylethyl, 4-(4-chlorophenoxy)phenylethyl, 4-pyrid-4-ylphenylpropyl, 4-pyrid-4-yloxyphenylethyl, 4-(4-chlorophenoxy) phenylethyl, 4-chlorophenylprop-2-ynyl, 4-biphenyl-4-ylprop-2-ynyl, and phenoxybutyl.

The Group $R_3$

In the compounds of the invention, $R_3$ may for example be $C_1$–$C_6$ alkyl, benzyl, 2,-3-, or 4-hydroxybenzyl, 2,-3-, or 4-benzyloxybenzyl, 2,-3-, or 4-$C_1$–$C_6$ alkoxybenzyl, or benzyloxy($C_1$–$C_6$alkyl)- group; or the characterising group of a natural a amino acid, in which any functional group may be protected, any amino group may be acylated and any carboxyl group present may be amidated; or a group a group —[Alk]$_n$R$_{10}$ where Alk is a ($C_1$–$C_6$)alkyl or ($C_2$–$C_6$)alkenyl group optionally interrupted by one or more —O—, or —S— atoms or —N(R$_{11}$)— groups [where R$_{11}$ is a hydrogen atom or a ($C_1$–$C_6$)alkyl group], n is 0 or 1, and R$_{10}$ is an optionally substituted cycloalkyl or cycloalkenyl group; or a benzyl group substituted in the phenyl ring by a group of formula —OCH$_2$COR$_{12}$ where R$_{12}$ is hydroxyl, amino, ($C_1$–$C_6$)alkoxy, phenyl($C_1$–$C_6$) alkoxy, ($C_1$–$C_6$)alkylamino, di(($C_1$–$C_6$)alkyl)amino, phenyl ($C_1$–$C_6$)alkylamino, the residue of an amino acid or acid halide, ester or amide derivative thereof, said residue being linked via an amide bond, said amino acid being selected from glycine, a or b alanine, valine, leucine, isoleucine, phenylalanine, tyrosine, tryptophan, serine, threonine, cysteine, methionine, asparagine, glutamine, lysine, histidine, arginine, glutamic acid, and aspartic acid.; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$) alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or a group —CR$_a$R$_b$R$_c$ in which:
each of R$_a$, R$_b$ and R$_c$ is independently hydrogen, ($C_1$–$C_6$) alkyl, ($C_2$–$C_6$)alkenyl, ($C_2$–$C_6$)alkynyl, phenyl($C_1$–$C_6$) alkyl, ($C_3$–$C_8$)cycloalkyl; or R$_c$ is hydrogen, ($C_1$–$C_6$)alkyl, ($C_2$–$C_6$)alkenyl, ($C_2$–$C_6$) alkynyl, phenyl($C_1$–$C_6$)alkyl, or ($C_3$–$C_8$)cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring (for example adamantyl); or R$_a$ and R$_b$ are each independently ($C_1$–$C_6$)alkyl, ($C_2$–$C_6$) alkenyl, ($C_2$–$C_6$)alkynyl, phenyl($C_1$–$C_6$)alkyl, or a group as defined for R$_c$ below other than hydrogen, or R$_a$ and R$_b$ together with the carbon atom to which they are attached form a cycloalkyl or heterocyclic ring, and R$_c$ is hydrogen, —OH, —SH, halogen, —CN, —CO$_2$H, ($C_1$–$C_4$)perfluoroalkyl, —CH$_2$OH, —CO$_2$ ($C_1$–$C_6$)alkyl, —O($C_1$–$C_6$)alkyl, —O($C_2$–$C_6$)alkenyl, —S($C_1$–$C_6$)alkyl, —SO($C_1$–$C_6$)alkyl, —SO$_2$($C_1$–$C_6$) alkyl, —S($C_2$–$C_6$)alkenyl, —SO($C_2$–$C_6$)alkenyl, —SO$_2$($C_2$–$C_6$)alkenyl or a group —Q—W wherein Q represents a bond or —O—, —S—, —SO—or —SO$_2$— and W represents a phenyl, phenylalkyl, ($C_3$–$C_8$)cycloalkyl, ($C_3$–$C_8$)cycloalkylalkyl, ($C_4$–$C_8$)

cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —$CO_2H$, —$CO_2$($C_1$–$C_6$)alkyl, —$CONH_2$, —CONH ($C_1$–$C_6$)alkyl, —CONH(($C_1$–$C_6$alkyl)$_2$, —CHO, —$CH_2OH$, ($C_1C_4$)perfluoroalkyl, —O($C_1$–$C_6$)alkyl, —S($C_1$–$C_6$)alkyl, —SO($C_1$–$C_6$)alkyl, —$SO_2$($C_1$–$C_6$) alkyl, —$NO_2$, —$NH_2$, —NH($C_1$–$C_6$)alkyl, —N(($C_1$–$C_6$)alkyl)$_2$, —NHCO($C_1$–$C_6$)alkyl, ($C_1$–$C_6$) alkyl, ($C_2$–$C_6$)alkenyl, ($C_2$–$C_6$)alkynyl, ($C_3$–$C_8$) cycloalkyl, ($C_4$–$C_8$)cycloalkenyl, phenyl or benzyl.

Examples of particular $R_3$ groups include benzyl, isobutyl, tert-butyl, 1-fluoro-1-methylethyl, 1-hydroxy-1-methylethyl, 1-methoxy-1-methylethyl, 1-benzylthio-1-methylethyl, 1-methylthio-1-methylethyl and 1-mercapto-1-methylethyl. Presently preferred are compounds in which $R_3$ is benzyl, t-butyl, 1-mercapto-1-methylethyl or 3H-imidazol-4-yl-methyl.

The Groups $R_4$ and $R_5$

In compounds of the invention wherein Y is a group (ID), $R_4$ may for example be cyclopropyl, cyclobutyl, cyclopentyl, cyclohexyl cycloheptyl or cyclooctyl;

optionally substituted phenyl, napthyl, furanyl, thienyl, pyrrolinyl, tetrahydrofuranyl, imidazolyl, oxadiazolyl, thiazolyl, thiadiazolyl, pyridinyl, pyridinyl N-oxides, piperazinyl, indolyl, benzimidazolyl, benzotriazolyl, pyrazinyl, pyridazinyl, pyrimidinyl, dithianyl, benzo[b] thienyl, isoxazolyl or quinolinyl. Examples of particular $R_4$ groups of this type include phenyl, 2-methoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulphonylphenyl, 3-methylsulphonylphenyl, 4-methylsulphonylphenyl, 2-trifluoromethylphenyl, 3-trifluoromethylphenyl, 4-trifluoromethylphenyl, 3,5-ditrifluoro-methylphenyl, 2-aminophenyl, 3-aminophenyl, 4-aminophenyl, 2-N,N-dimethylaminophenyl, 3-N,N-dimethylaminophenyl, 4-N,N-dimethylaminophenyl, 2-hydroxyphenyl, 3-hydroxyphenyl, 4-hydroxyphenyl, 2-napthyl, furan-2-yl, thien-2-yl, pyrrol-2-yl, tetrahydrofuran-2-yl, imidazol-2-yl, thiazol-2-yl, 4-ethoxycarbonyl-methylthiazol-2-yl, 4-phenylthiazol-2-yl, 4,5-dimethylthiazol-2-yl, 5-bromothiazol-2-yl, 4-tert-butylthiazol-2-yl, benzothiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1,2,4-thiadiazol-5-yl, 1,3,4-thiadiazol-2-yl, 5-methyl-1,3,4-thiadiazol-2-yl, pyridin-2-yl, pyridin-3-yl, pyridin-4-yl, N-oxides of pyridin-2-yl pyridin-3-yl and pyridin4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo[b]thien-2-yl, isoxazol-5-yl, quinolin-3-yl. Presently preferred are compounds in which $R_4$ is phenyl, 3-methoxyphenyl, pyridin-2-yl, pyridin-3-yl, and thiazol-2-yl, 4,5-dimethylthiazol-2-yl, 5-bromothiazol-2-yl, 4-ethoxycarbonylmethylthiazol-2-yl, 5-methyl-1,3,4-thiadiazol-2-yl or 4-tertbutylthiazol-2-yl. Particularly preferred $R_4$ groups of this type are 3-methoxyphenyl, pyridin-2-yl, pyridin-3-yl, pyridin-4-yl, thiazol-2-yl, 4-ethoxycarbonylmethylthiazol-2-yl, 5-methyl-1,3,4-thiadiazol-2-yl or 4-tert-butylthiazol-2-yl;

a group —$CHR^xR^y$ wherein $R^x$ and $R^y$ independently represent optionally substituted phenyl, thienyl, furyl, pyrrolyl, imidazolyl, thiazolyl, pyrazolyl, isoxazolyl, isothiazolyl, triazolyl, thiadiazolyl, oxadiazolyl, pyridinyl, pyridazinolyl, pyrimidinyl, piperazinyl or triazinyl. Examples of particular $R^x$ and $R^y$ include phenyl, 4-chlorophenyl and pyridinyl. Where $R^x$ and $R^y$ are linked covalently, an example of a group $R_4$ is 9-H-fluoren-9-yl;

a polyether chain possessing at least two non-adjacent oxygen atoms, for example 2-(2-methoxyethoxymethoxy)ethyl, 1,1-dimethyl-2-(2-methoxyethoxymethoxy)ethyl, 2-(2-ethoxyethoxymethoxy)ethyl, 2-(2-(2-methoxyethoxy)ethoxy)ethyl, 2-($^2$-(3-methoxypropoxymethoxy)ethyl, 3-(2-methoxyethoxymethoxy)propyl, 2,2-dimethyl-3-(2-methoxyethoxymethoxy)propyl, 2-(2-methoxyethoxy)ethyl, 3-(2-methoxyethoxy)-propyl, 2-methyl-2,2-di(2-methoxyethyl)propyl, 2-methyl-2,2-di(2-methoxyethyl)butyl, and 2-methyl-2,2-di(2-methoxymethyl)propyl. A presently preferred $R_4$ group of this type is 2-(2-methoxyethoxy)ethyl;

methyl, ethyl, n- or iso-propyl, n-, sec- or tert-butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone)propyl, morpholin-4-ylpropyl, optionally substituted phenylethyl, phenylpropyl, phenylbutyl, or phenylpentyl. Presently preferred $R_4$ groups of this type are hydrogen, methyl or morpholin-4-ylpropyl.

In compounds of the invention wherein Y is a group (ID), where $R_3$ and $R_4$ taken together represent a divalent chain of formula —C($R^a$)($R^b$)—A—Alk— wherein $R^a$ and $R^b$ are independently hydrogen or $C_1$–$C_6$ alkyl, A is a bond, —O—, —S—, —S—S—, —NH— or —$NR^a$— wherein $R^a$ is $C_1$–$C_6$ alkyl, and Alk is $C_1$–$C_6$ alkylene, examples of such divalent chains include —C($CH_3$)$_2$$SCH_2CH_2CH_2$—, and —C($CH_3$)$_2$$SSCH_2CH_2$—.

In compounds of the invention wherein Y is a group (ID), examples of particular $R_5$ groups include hydrogen, methyl and ethyl. Presently preferred are compounds in which $R_5$ is methyl.

In one particular class of compounds of the invention wherein Y is a group (ID), $R_4$ and $R_5$ are both methyl.

The Groups $R_6$ and $R_7$

In compounds of the invention wherein Y is a group (IE), $R_6$ may be, for example, hydrogen, methyl, ethyl, benzyl or pyridylmethyl, and $R_7$ may be, for example hydrogen or methyl. $R_6$ and $R_7$ taken together with the carbon atom to which they are attached may form, for example, a cyclopentyl, cyclohexyl or morpholino ring. Presently preferred are compounds in which $R_6$ and $R_7$ are both hydrogen.

In compounds of the invention wherein Y is a group (IE), when $R_7$ is hydrogen, $R_3$ and $R_6$ taken together with the carbon atoms to which they are attached may form a 2-hydroxycyclohexyl or a glucose ring.

The Group $R_8$ $R_8$ may for example be hydrogen, methyl, ethyl, n- or iso-propyl, n-, sec- or tert-butyl, n-pentyl, n-hexyl, benzyl, or acetyl. Presently preferred are compounds in which $R_8$ is hydrogen, acetyl or methyl.

The Group $R_9$ $R_9$ may for example be substituted or unsubstituted methyl, ethyl, n- or iso-propyl, n-, sec- or tert-butyl, n-pentyl, n-hexyl, cyclopropyl, cyclobutyl, cyclopentyl, cyclohexyl, cycloheptyl, cyclooctyl, cyclopentenyl, cyclohexenyl, cycloheptenyl, cyclooctenyl, di-($C_1$–$C_6$ alkyl)amino such as dimethyl- or diethyl-amino, phenyl, naphthyl, thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl or triazinyl. Specific examples of substituted $R_9$ groups include benzyl, 2-methoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulfonylphenyl, 3-methylsulfonylphenyl, 4-methylsulfonylphenyl, 2-trifluoromethylphenyl, 3-trifluoromethylphenyl, 4-trifluoromethylphenyl, 3,5-ditrifluoromethylphenyl, 2-aminophenyl, 3-aminophenyl, 4-aminophenyl, 2-N,N-dimethylaminophenyl, 3-N,N-dimethylaminophenyl, 4-N,N-dimethylaminophenyl, 2-hydroxyphenyl, 3-hydroxyphenyl, 4-hydroxyphenyl, naphth-1-yl and naphth-2-yl; furan-2-yl, thien-2-yl, imidazol-2-yl, thiazol-2-yl, 4-ethoxycarbonylmethyl-thiazol-2-yl, 4-phenylthiazol-2-yl, 4,5-dimethylthiazol-2-yl, 5-bromothiazol-2-yl, 4-tert-butylthiazol-2-yl, benzothiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1,2,4-thiadiazol-5-yl, 1,3,4-thiadiazol-2-yl, 5-methyl-1,3,4-thiadiazol-2-yl, pyridin-2-yl, pyridin-3-yl, pyridin-4-yl, N-oxides of pyridin-2-yl, pyridin-3-yl and pyridin-4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo[b]thien-2-yl, isoxazol-5-yl, and quinolin-3-yl. Presently preferred are compounds in which $R_9$ is methyl, dimethylamino, trifluoromethyl, phenyl, 4-methoxyphenyl, 4-chlorophenyl, naphth-1-yl, naphth-2-yl or thien-2-yl.

$R_8$ and $R_9$ taken together with the N and S atoms to which they are attached may represent a group of formula (XI) or (XII)

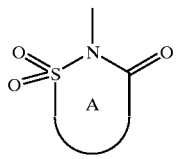

(XI)

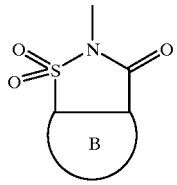

(XII)

wherein ring A is a substituted or unsubstituted, saturated or unsaturated 5–8 membered ring and ring B is a substituted or unsubstituted fused phenyl orheteroaryl (e.g. thienyl or pyridinyl) ring.

Specific compounds of the invention include:

$N^4$-(1S-dimethylaminocarbamoyl-2,2-dimethyl-propyl)-$N^1$-hydroxy-3R-isobutyl-2R-[(methanesulfonyl-methyl-amino)-methyl]-succinamide, $N^1$-hydroxy-3R-isobutyl-2R-[(methanesulfonyl-methyl-amino)-methyl]-$N^4$-{1S-[2-(2-methoxy-ethoxy)-ethyl-carbamoyl]-2,2-dimethyl-propyl}-succinamide, $N^4$-(1S-benzyl-2-hydroxy-ethyl)-$N^1$-hydroxy-3R-isobutyl-2R-[(methanesulfonyl-methyl-amino)methyl]-succinamide, $N^1$-hydroxy-$N^4$-(1S-hydroxymethyl-2,2-dimethylpropyl)-3R-isobutyl-2R-[(methanesulfonyl-methyl-amino)-methyl]-succinamide, $N^1$-hydroxy-$N^4$-[2-hydroxy-1S-(1H-imidazol-4-ylmethyl)ethyl]-3R-isobutyl-2S-[(methanesulfonyl-methyl-amino)-methyl]-succinamide, $N^1$-hydroxy-$N^4$-[2-hydroxy-1S-(4-hydroxy-benzyl)-ethyl]-3R-isobutyl-2S-[(methanesulfonyl-methyl-amino)methyl]-succinamide, $N^4$-(1S-dimethylcarbamoyl-2,2-dimethyl-propyl)-$N^1$-hydroxy-3R-isobutyl-2S-{[(4-methoxy-benzenesulfonyl)-methyl-amino]-methyl}-succinamide, $N^4$-(1S-benzyl-2-hydroxy-ethyl)-$N^1$-hydroxy-3R-isobutyl-2S-{[(4-methoxy-benzenesulfonyl)-methyl-amino]-methyl}succinamide, 3R-(3-biphenyl4-yl-propyl)-$N^1$-hydroxy-$N^4$-[2S-hydroxy-1-(1H-imidazol-4-ylmethyl)-ethyl]-2S-{[(4-methoxy-benzenesulfonyl)-methyl-amino]-methyl}-succinamide, 3R-cyclopentylmethyl-$N^1$-hydroxy-$N^4$-(1S-hydroxymethyl-2,2-dimethyl-propyl)-2S-{[(4-methoxy-benzenesulfonyl)-methyl-amino]-methyl}-succinamide, 3R-cyclopentylmethyl-2S-{[(5-dimethylamino-naphthalene-1-sulfonyl)methyl-amino]-methyl}-$N^1$-hydroxy-$N^4$-(1S-hydroxymethyl-2,2-dimethyl-propyl)-succinamide, $N^1$-(1S-benzyl-2-hydroxy-ethyl)-3R-(3-biphenyl-4-yl-propyl)-$N^1$-hydroxy-2S-[(methanesulfonyl-methyl-amino)-methyl]-succinamide, 3R-(3-biphenyl-4-yl-propyl)-$N^1$-hydroxy-$N^4$-(1S-hydroxymethyl-2,2dimethyl-propyl)-2S-{[(4-methoxy-benzenesulfonyl)-methyl-amino]-methyl}succinamide, $N^4$-(1S-benzyl-2-hydroxy-ethyl)-3R-(3-biphenyl-4-yl-propyl)-$N^1$-hydroxy-2S-{[(4-methoxy-benzenesulfonyl)-methyl-amino]-methyl}-succinamide and pharmaceutically acceptable salts, hydrates and solvates thereof.

Compounds of the invention wherein X is HONH— may be prepared by a process which comprises causing an acid of the invention of general formula (II)

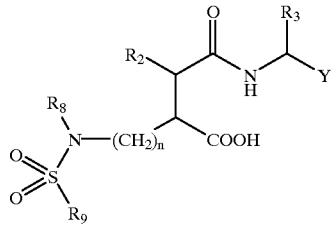

(II)

or an activated derivative thereof to react with hydroxylamine, O-protected hydroxylamine, N,O-diprotected hydroxylamine, or a salt thereof, n, Y, $R_2$, $R_3$, $R_8$, and $R_9$, being as defined in general formula (I) except that any substituents in Y, $R_2$, $R_3$, $R_8$, and $R_9$ which are potentially reactive with hydroxylamine, the O-protected hydroxylamine, the N,O-iprotected hydroxylamine or their salts may themselves be protected from such reaction, then removing any protecting groups from the resultant hydroxamic acid moiety and from any protected substituents in Y, $R_2$, $R_3$, $R_8$, and $R_9$.

Conversion of (II) to an activated derivative such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in the process of the invention above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in the process of the invention include N,O-bis(benzyl)hydroxylamine, N,O-bis(4-methoxybenzyl)hydroxylamine, N-tert-butoxycarbonyl-O-tert-butyldimethylsilylhydroxylamine, N-tert-butoxycarbonyl-O-tetrahydropyranylhydroxylamine, and N,O-bis(tert-butoxycarbonyl)hydroxylamine.

Acids of the invention (II) may be prepared by forming the appropriate $R_9$-sulfonamide of an amine of formula (III), for example by reaction with an activated derivative of a sulphonic acid (IV),

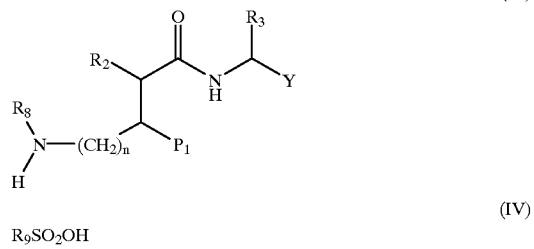

(III)

(IV)

$R_9SO_2OH$ wherein $P_1$ is a protected carboxyl group and n, Y, $R_2$, $R_3$ and $R_8$ are as defined in relation to formula (I) except that any substituents in Y, $R_2$, $R_3$ and $R_8$ which are potentially reactive with (IV) may be protected, and thereafter deprotecting the protected carboxyl group $P_1$ and any protected substituents in Y, $R_2$, $R_3$, and $R_8$. Activated sulphonic acids and conditions for forming sulfonamides are well known in organic synthesis, e.g. reaction with the sulfonyl chloride in the presence of an organic base.

Amines of formula (III) in which $R_8$ is hydrogen may be prepared from the corresponding hydroxyl compound of formula (IIIA)

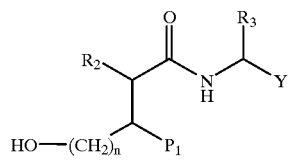

(IIIA)

by methods known in organic synthesis for conversion of hydroxyl groups to amine groups, e.g. by conversion the hydroxyl group of (IIIA) to a leaving group, displacement with azide, followed by catalytic hydrogenation of the azide group.

Amines of formula (III) in which $R_8$ is other than hydrogen may be accessible by direct introduction of $R_8$ onto the amine group of the compound (III) wherein $R_8$ is hydrogen. In the special case of compounds (III) wherein n is 1, ammination of the double bond of compounds (V)

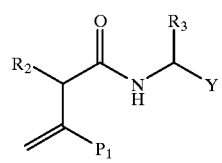

(V)

with the amine $R_8NH_2$ can provide a convenient route.

Compounds (IIIA) and (V) may be prepared by reaction of an amine (VI)

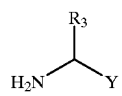

(VI)

wherein Y and $R_3$ are as defined in relation to formula (IIIA), with the corresponding carboxylic acids (VII) or (VIII)

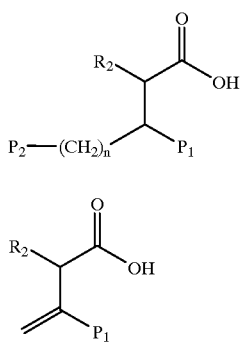 (VII)

 (VIII)

wherein n, $P_1$ and $R_2$ are as defined in relation to formula (IIIA) and $P_2$ is a protected hydroxyl group, which is converted to the required hydroxyl group after the reaction with amine (VI).

Amino acid amides and amino alcohols of formula (VI, and ) compounds (VII) and (VIII) are either known, are analogues of known compounds, or are accessible by known literature methods. For example, compounds of formula (VII) and (VIII) wherein $R_2$ is a triple unsaturated radical of formula (B) above may in many cases be prepared by alkylation of a the corresponding carboxyl protected compound ($R_2$=hydrogen) with a halide of formula (IX)

$$H-(C\equiv C)_r-(CH_2)_s-L \qquad (IX)$$

wherein r and s are as defined in relation to formula (B) and L is a reactive halo group (eg bromo) capable of reacting with (VII) or (VIII) at the C atom adjacent the protected carboxyl group with elimination of the elements of HL and then reacting the resultant compound with a halide Ar—L, wherein Ar is as defined in relation to formula (B) and L is again a reactive halo group, under palladium catalysis (the Heck reaction; see R. F. Heck, *Palladium Reagents in Organic Synthesis,* Academic Press, London 1985), again with elimination of the elements of HL. The terminal hydrogen of compound (IX) may optionally be protected during the reaction, for example as a silyl derivative such as trimethylsilyl.

As mentioned above, compounds of formula (I) are useful in human or veterinary medicine since they are active as inhibitors of MMPs.

Accordingly in another aspect, this invention concerns:

(i) a method of management (by which is meant treatment or prophylaxis) of diseases or conditions mediated by MMPs in mammals, in particular in humans, which method comprises administering to the mammal an effective amount of a compound as defined with respect to formula (I) above, or a pharmaceutically acceptable salt thereof; and (ii) a compound as defined with respect to formula (I) for use in human or veterinary medicine, particularly in the management (by which is meant treatment or prophylaxis) of diseases or conditions mediated by MMPs; and (iii) the use of a compound as defined with respect to formula (I) in the preparation of an agent for the management (by which is meant treatment or prophylaxis) of diseases or conditions mediated by MMPs.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases as well as neuroinflammatory disorders, including those involving myelin degradation, for example multiple sclerosis.

In a further aspect of the invention there is provided a pharmaceutical or veterinary composition comprising a compound of formula (I) together with a pharmaceutically or veterinarily acceptable excipient or carrier.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 5 to 100 mg of a compound of the invention. A suitable daily dose for a mammal may vary widely depending on the condition of the patient. However, a dose of a compound of general formula I of about 0.1 to 10 mg/kg body weight, particularly from about 0.1 to 3 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articulaey into the affected joint.

The following Examples illustrate embodiments of the invention.

2-Benzyloxycarbonyl-3R-carboxy-5-methyl-hexanoic acid 1-benzyl ester 4-tert-butyl ester was prepared as described in EP 0 446 267. L-tert-leucine-N-2-(2-methoxy-ethoxy) ethylamide was prepared as described in WO 96/16931. L-tert-leucine-N,N-dimethylamide was prepared by a similar method. 3R-cyclopentylmethyl-succinic acid 1-benzyl ester 4-tert-butyl ester was prepared by Evans' methodology, as described in WO 92/13831. The following abbreviations have been used throughout:

| | |
|---|---|
| DMF | N,N-Dimethylformamide |
| EDC | N-Ethyl-N'-(3-dimethylaminopropyl)-carbodiimide |
| HOBt | 1-Hydroxybenzotriazole |
| LDA | Lithium diisopropylamide |
| NMM | N-Methylmorpholine |
| TFA | Trifluoroacetic acid |
| THF | Tetrahydrofuran |
| TLC | Thin Layer Chromatography |

$^1$H and $^{13}$C NMR spectra were recorded using a Bruker AC 250E spectrometer at 250.1 and 62.9 MHz, respectively. Infra red spectra were recorded using a Perkin Elmer 1600 Series FTIR spectrometer. Elemental microanalyses were performed by Medac Ltd. (Department of Chemistry, Brunel University, Uxbridge, Middlesex UB8 3PH).

EXAMPLE 1

$N^4$-(1S-Dimethylamino-2,2-dimethyl-propyl)-$N^1$-hydroxy-3R-isobutyl-2R-[(methanesulfonyl-methyl-amino)-methyl]-succinamide

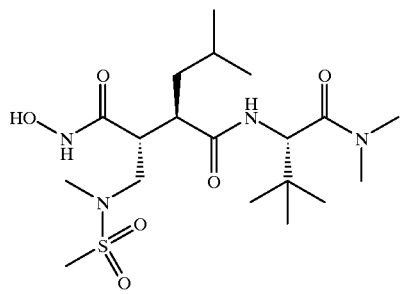

The title compound was prepared according to the route outlined in Scheme 1 and is described in detail below.

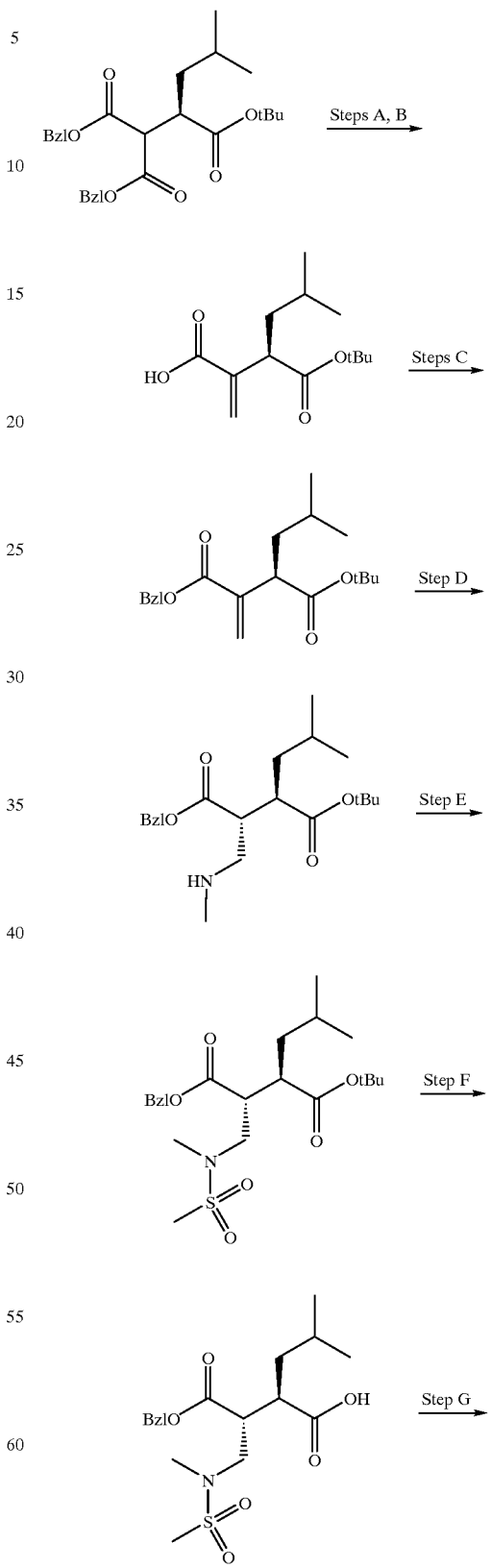

Scheme 1

-continued

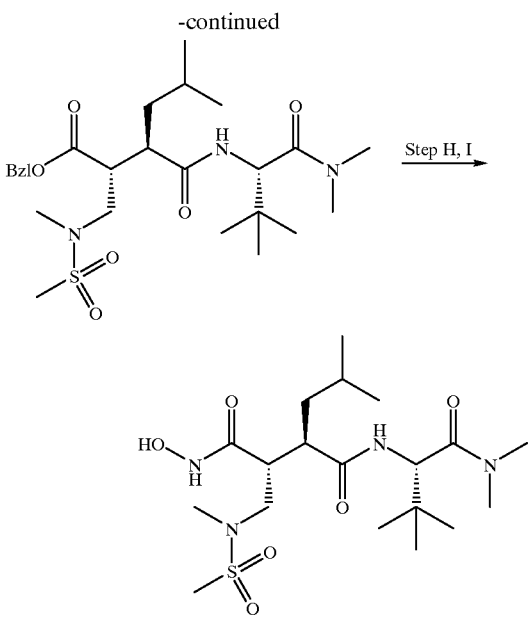

Reagents and conditions: (A) H$_2$, 10% Pd/C in EtOAc; (B) piperidine aq. HCHO in ethanol; (C) Bzl-Br, K$_2$CO$_3$ in acetone; (D) MeNH$_2$ in methanol; (E) MsCl, Et$_3$N, CH$_2$Cl$_2$; (F) TFA, CH$_2$Cl$_2$, 4° C.; (G) H-Tle-NMe$_2$, EDC, HOBt in EtOAc; (H) H$_2$, 10% Pd/C in EtOAc; (I) HOBt, EDC in DMF, then H$_2$NOH, HCl, NMM.

Step A: 2-Carboxy-3R-isobutyl-succinic acid 4-tert-butyl ester

2-Benzyloxycarbonyl-3R-carboxy-5-methyl-hexanoic acid 1-benzyl ester 4-tert-butyl ester (55.53 g, 126 mmol) was dissolved in ethyl acetate (500 ml) and the solution was placed under an argon atmosphere. 10% Palladium on charcoal (5.55 g) was added and the resulting suspension was placed under an atmosphere of hydrogen. After stirring for 3 days, TLC analysis indicated that deprotection was complete. The catalyst was removed by filtration and the solution was concentrated under reduced pressure to leave the title compound as a clear oil (ca. 33 g, quant.), which was used without further purification. $^1$H-NMR: δ(CDCl$_3$), 3.73 (1H, d, J=9.1 Hz), 3.09 (1H, m), 1.75–1.58 (2H, m), 1.45 (9H, s), 1.31 (1H, m), 0.96 (3H, d, J=6.5 Hz) and 0.92 (3H, d, J=6.5 Hz).

Step B: 3R-Isobutyl-2-methylene-succinic acid 4-tert-butyl ester

2-Carboxy-3R-isobutyl-succinic acid 4-tert-butyl ester (33 g, 126 mmol) was dissolved in ethanol (300 ml) and the solution was cooled in an ice bath during dropwise addition of piperidine (14.95 ml, 151 mmol) followed by 37% aqueous formaldehyde solution (47.17 ml, 630 mmol). The reaction mixture was allowed to warm to room temperature then stirred overnight. The solvent was removed by evaporation and the residue was redissolved in ethyl acetate, washed successively with 1M hydrochloric acid (400 ml) and brine (400 ml), dried over anhydrous sodium sulfate and filtered. The solution was concentrated under reduced pressure to leave the title compound as a colourless oil (28.11 g, 97%). $^1$H-NMR: δ(CDCl$_3$), 6.46 (1H, s), 5.84 (1H, s), 3.50 (1H, t, J=6.3 Hz), 1.85–1.40 (3H, m), 1.45 (9H, s), 0.95 (3H, d, J=6.9 Hz) and 0.93 (3H, d, J=6.9 Hz).

Step C: 3R-Isobutyl-2-methylene-succinic acid 1-benzyl ester 4-tert-butyl ester 3R-Isobutyl-2-methylene-succinic acid 4-tert-butyl ester (28.11 g, 122 mmol) was dissolved in acetone (500 ml) and the solution was placed under an argon atmosphere. Solid potassium carbonate (67.34 g, 488 mmol) was added and the suspension was stirred for 30 minutes. Benzyl bromide (13.13 ml, 110 mmol) was added and the reaction mixture was left to stir overnight at room temperature. The inorganics were removed by filtration and the solvent was removed under reduced pressure to leave the title compound as a yellow oil (35.5 g, ca. 91%; trace benzyl bromide). $^1$H-NMR: δ(CDCl$_3$), 7.45–7.28 (5H, m), 6.37 (1H, s), 5.75 (1H, s), 5.22 (2H, s), 3.55 (1H, t, J=6.9 Hz), 1.75–1.35 (3H, m), 1.40 (9H, s) and 0.90 (6H, t, J=6.5 Hz).

STEP D: 3R-Isobutyl-2R-methylaminomethyl-succinic acid 1-benzyl ester 4-tert-butyl ester Methylamine (8.03 M solution in ethanol; 9.19 ml, 74.3 mmol) was added to a stirred solution of 3R-isobutyl-2-methylene-succinic acid 1-benzyl ester 4-tert-butyl ester (11.89 g, 37.2 mmol) in methanol (60 ml) and the mixture was stirred at room temperature for 2 hours. The solvent was removed in vacuo to leave the title compound as a yellow oil (12.82 g, 95%). $^1$H-NMR: δ(CDCl$_3$), 7.24 (5H, m), 5.05 (2H, m), 2.78 (2H, m), 2.53 (2H, m), 2.27 (3H, s), 1.51 (2H, m), 1.31 (9H, s), 0.78 (1H, m), 0.72 (3H, d, J=6.4 Hz) and 0.69 (3H, d, J=6.4 Hz).

STEP E: 3R-Isobutyl-2R-[(methanesulfonyl-methyl-amino)-methyl]-succinic acid 1-benzyl ester 4-tert-butyl ester 3R-isobutyl-2R-methylaminomethyl-succinic acid 1-benzyl ester 4-tert-butyl ester (12.82 g, 35.4 mmol) was dissolved in dry dichloromethane (100 ml) and the solution was cooled to 0° C. Triethylamine (9.87 ml, 70.8 mmol) was added followed by methanesulfonyl chloride (2.60 ml, 33.6 mmol) and the reaction mixture was allowed to warm slowly to room temperature then stirred for 3 hours. The solvents was removed under reduced pressure and the residue was dissolved in ethyl acetate (150 ml). The organic solution was washed successively with water, 1M sodium carbonate solution and 10% citric acid solution, dried over anhydrous sodium sulfate, filtered and concentrated in vacuo to leave the title compound (13.62 g, 87%) which was used without further purification. $^1$H-NMR: δ(CDCl$_3$), 7.49 (5H, m), 5.29 (1H, d, J=12.0 Hz), 5.24 (1H, d, J=12.0 Hz), 3.50 (1H, dd, J=9.2, 13.2 Hz), 3.25 (1H, d, J=5.1, 13.2 Hz), 3.05 (1H, m), 2.85 (3H, s), 2.78 (3H, m), 2.65 (1H, m), 1.63 (2H, m), 1.47 (9H, s), 1.01 (1H, m) and 0.85 (6H, m).

STEP F: 3R-Isobutyl-2R-[(methanesulfonyl-methyl-amino)-methyl]-succinic acid 1-benzyl ester 3R-isobutyl-2R-[(methanesulfonyl-methyl-amino)-methyl]-succinic acid 1-benzyl ester 4-tert-butyl ester (13.62 g, 30.95 mmol) was dissolved in dichloromethane (25 ml) and TFA (24 ml) was added. The reaction mixture was stored at 4° C. overnight. The solvent was removed under reduced pressure and residual TFA was removed by azeotroping with toluene followed by dichloromethane. The crude product was recrystallised from diethyl ether-hexane to provide the desired compound as an off-white solid (9.83 g, 83%). $^1$H-NMR: δ(CDCl$_3$), 9.60 (1H, br s), 7.42 (5H, m), 5.28 (1H, d, J=12.0 Hz), 5.22 (1H, d, J=12.0 Hz), 3.53 (1H, dd, J=9.4, 13.8 Hz), 3.34 (1H, dd, J=5.4, 13.8 Hz), 3.15 (1H, m), 2.84 (3H, m), 2.81 (1H, m), 2.79 (3H, m), 1.66 (2H, m), 1.13 (1H, m) and 0.88 (6H, m).

STEP G: 3R-(1S-Dimethylcarbamoyl-2,2-dimethyl-propyl-carbamoyl)-2R-[(methanesulfonyl-methyl-amino)-methyl]-5-methyl-hexanoic acid benzyl ester 3R-isobutyl-2R-[(methanesulfonyl-methyl-amino)-methyl]-succinic acid 1-benzyl ester (857 mg, 2.2 mmol), HOBt (362 mg, 2.7 mmol) and EDC (513 g, 2.7 mmol) were dissolved in ethyl acetate (60 ml) and the mixture was heated at reflux for 2 hours. L-tert-leucine N,N-dimethylamide(388 mg, 2.5 mmol) was added and the mixture was heated at reflux for a further 3 hours then stirred at room temperature overnight. The solution was washed successively with 1M hydrochloric acid and 1M sodium carbonate solution, dried over anhydrous magnesium sulphate and filtered. The solvent was removed under reduced pressure to leave the title compound as an off-white foam (853 mg, 73%). $^1$H-NMR: $\delta$(CDCl$_3$), 7.29 (5H, m), 6.29 (1H, d, J=9.2 Hz), 5.16 (1H, d, J=12.0 Hz), 5.04 (1H, d, J=12.0 Hz), 4.78 (1H, d, J=9.3 Hz), 3.50 (1H, m), 3.05 (3H, s), 3.00 (1H, m), 2.85 (3H, s), 2.76 (1H, m), 2.72 (3H, s), 2.64 (3H, s), 2.49 (1H, m), 1.51 (1H, m), 1.32 (1H, m), 1.02 (1H, m), 0.90 (9H, s) and 0.70 (6H, m).

STEP H: 3R-(1S-Dimethylcarbamoyl-2,2-dimethyl-propyl-carbamoyl)-2R-[(methanesulfonyl-methyl-amino)-methyl]-5-methyl-hexanoic acid 3R-(1S-Dimethylcarbamoyl-2,2-dimethyl-propyl-carbamoyl)-2R-[(methanesulfonyl-methyl-amino)-methyl]-5-methyl-hexanoic acid benzyl ester (853 mg, 1.63 mmol) was dissolved in ethanol (100 ml) and subjected to hydrogenolysis in the presence of 10% palladium on charcoal (300 mg) under conditions similar to those described in Step A. After 6 hours the catalyst was removed by filtration and the solvent was removed under reduced pressure to leave the desired carboxylic acid as a white foam (686 mg, 97%). $^1$H-NMR: $\delta$(CDCl$_3$), 7.97 (1H, m), 4.95 (1H, d, J=9.5 Hz), 3.51 (1H, m), 3.12 (3H, s), 3.08 (1H, m), 2.86 (3H, s), 2.84 (1H, m), 2.75 (3H, s), 2.69 (3H, s), 2.67 (1H, m), 1.61 (1H, m), 1.33 (1H, m), 1.17 (1H, m), 0.94 (9H, s), 0.78 (3H, d, J=6.8 Hz) and 0.74 (3H, d, J=6.7 Hz).

STEP I: N$^4$-(1S-Dimethylamino-2,2-dimethyl-propyl)-N$^1$-hydroxy-3R-isobutyl-2R-[(methane sulfonyl-methyl-amino)-methyl]-succinamide 3R-(1S-Dimethylcarbamoyl-2,2-dimethyl-propyl-carbamoyl)-2R-[(methanesulfonyl-methyl-amino)-methyl]-5-methyl-hexanoic acid (686 mg, 1.6 mmol) was dissolved in DMF (40 ml) and the solution was cooled to 0° C. before addition of HOBt (256 mg, 1.89 mmol) and EDC (364 mg, 1.89 mmol). The reaction mixture was stirred for 30 minutes after which hydroxylamine hydrochloride (165 mg, 2.37 mmol) and NMM (261 μl, 2.37 mmol) were added. The reaction mixture was allowed to warm to room temperature and then stirred overnight. The solvent was removed in vacuo and the residue was purified by flash chromatography (acid-washed silica gel, 5% methanol in dichloromethane) to give the desired product contaminated with HOBt. Trituration with ethyl acetate gave the title compound as a white solid (296 mg, 42%).

White solid. m.p. 216–218° C. $^1$H-NMR: $\delta$(CD$_3$OD), 8.18 (1H, d, J=8.6 Hz), 4.92 (1H, s), 3.51 (1H, dd, J=10.9, 13.6 Hz), 3.22 (3H, s), 3.05 (1H,dd, 3.6, 13.7 Hz), 2.95 (3H, s), 2.82 (6H, s), 2.71 (1H, dd, 3.5, 10.8 Hz), 1.57 (1H, m), 1.39 (1H, m), 1.13 (1H, m), 1.08 (9H, s), 0.89 (3H, d, J=6.5 Hz), and 0.84 (3H, d, J=6.5 Hz). $^{13}$C-NMR: $\delta$(Cd$_3$OD): 174.9, 171.9, 170.1, 55.7, 50.9, 46.6, 44.7, 40.4, 37.8, 35.0, 34.9, 26.2, 25.9, 23.3 and 20.9. IR: $v_{max}$(KBr), 3278, 2957, 1634, 1520, 1398, 1337, 1148, 968, 781 and 520 cm$^{-1}$. Found: C, 50.60; H, 8.57; N, 12.34%. C$_{19}$H$_{38}$N$_4$O$_6$S requires C, 50.65; H, 8.50; N, 12.43%.

The compounds of Examples 2–6 were prepared by analogy with Example 1, substituting the appropriate amino acid derivative or amino alcohol for L-tert-leucine N,N-dimethylamide in Step G:

EXAMPLE 2

N$^1$-Hydroxy-3R-isobutyl-2R-[(methanesulfonyl-methyl-amino)-methyl]-N$^4$-{1S-[2-(2-methoxy-ethoxy)-ethyl-carbamoyl]-2,2-dimethyl-propyl}-succinamide

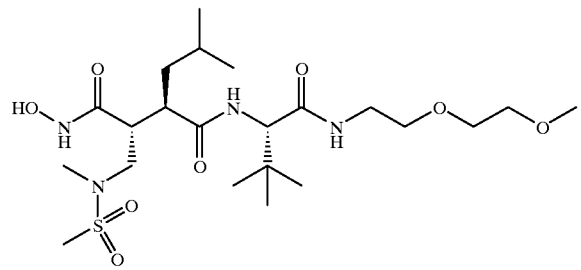

White solid. m.p. 192–193° C. $^1$H-NMR: $\delta$(CD$_3$OD): 8.00 (1H, m), 7.92 (1H, d, J=9.1 Hz), 4.23 (1H, d, J=9.1 Hz), 3.47 (8H, br m), 3.25 (3H, s), 3.21 (1H, m), 2.92 (1H, dd, J=13.7, 3.5 Hz), 2.69 (3H, s), 2.68 (3H, s), 2.63 (1H, m), 2.48 (1H, m), 1.41 (1H, m), 1.29 (1H, m), 1.01 (1H, m), 0.93 (9H, s), 0.77 (3H, d, J=6.5 Hz) and 0.72 (3H, d, J=6.5 Hz). $^{13}$C-NMR: $\delta$(CD$_3$OD): 178.0, 174.7, 173.4, 75.4, 73.4, 72.9, 64.8, 61.6, 54.3, 48.3, 43.9, 42.6, 38.4, 37.6, 29.9, 29.3, 26.8 and 24.3. IR: $v_{max}$(KBr), 3312, 2955, 1635, 1534, 1469, 1337, 1146, 970 and 782 cm$^{-1}$. Found: C, 49.50; H, 8.43; N, 10.52%. C$_{22}$H$_{44}$N$_4$O$_8$S.0.5H$_2$O requires C, 49.50; H, 8.50; N, 10.50%.

EXAMPLE 3

N$^4$-(1S-Benzyl-2-hydroxy-ethyl)-N$^1$-hydroxy-3R-isobutyl-2R-[(methanesulfonyl-methyl-amino)-methyl]-succinamide

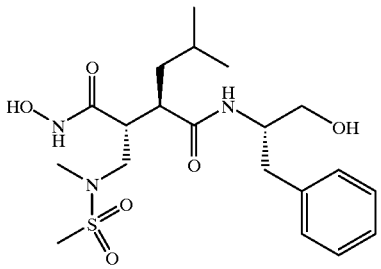

White solid. m.p. 200–202° C. $^1$H-NMR: $\delta$(CD$_3$OD), 8.14 (1H, d, J=8.7 Hz), 7.28 (5H, m), 4.25 (1H, m), 3.58 (1H, dd, J=5.1, 10.7 Hz), 3.49 (1H, dd, J=6.2, 10.7 Hz), 3.21 (1H, m), 3.06 (1H, dd, J=4.3, 13.9 Hz), 2.70 (3H, s), 2.66 (1H, m), 2.57 (3H, s), 2.37 (2H, m), 2. 12 (1H, m), 1.50 (2H, m), 1.01 (1H, m), 0.86 (3H, d, J=6.7 Hz) and 0.84 (3H, d, J=6.7 Hz). $^{13}$C-NMR: $\delta$(CD$_3$OD): 174.4, 170.2, 139.3, 129.4, 128.5, 126.6, 64.2, 53.7, 50.3, 46.1, 45.1, 40.4, 36.9, 36.2, 34.3, 25.8, 23.5 and 20.6. IR: $v_{max}$(KBr), 3322, 3223, 2960, 2874, 1668, 1634, 1563, 1533, 1455, 1321, 1217, 1152, 1044, 970 and 703 cm$^{-1}$. Found: C, 52.53; H, 7.61; N, 9.64%. C$_{20}$H$_{33}$N$_3$O$_6$S.0.6H$_2$O requires C, 52.87; H, 7.59; N, 9.25%.

EXAMPLE 4

N$^1$-Hydroxy-N$^4$-(1S-hydroxymethyl-2,2-dimethylpropyl)-3R-isobutyl-2R-[(methanesulfonyl-methyl-amino)-methyl]-succinamide

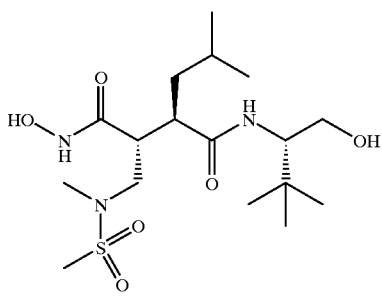

Off-white solid. m.p. 167–169° C. $^1$H-NMR: δ((CD$_3$)$_2$SO), 10.66 (1H, s), 8.95 (1H, s), 7.64 (1H, d, J=9.2 Hz), 4.32 (1H, m), 3.63 (1H, m), 3.51 (2H, m), 3.35 (1H, s), 3.23 (1H, m), 2.78 (1H, m), 2.73 (3H, s), 2.66 (3H, s), 2.51 (1H, m), 1.47 (2H, m), 0.89 (9H, s), 0.85 (1H, m), 0.81 (3H, d, J=6.4 Hz) and 0.78 (3H, d, J=6.6 Hz). $^{13}$C-NMR: δ((CD$_3$)$_2$ SO): 173.3, 168.5, 61.6, 59.1, 50.6, 45.1, 44.8, 35.3, 34.9, 33.7, 27.6, 25.0 and 21.8. IR: ν$_{max}$(KBr), 3206, 2959, 1641, 1555, 1467, 1369, 1331, 1265, 1215, 1151, 969 and 786 cm$^{-1}$. Found: C, 49.11; H, 8.29; N, 10.01%. C$_{17}$H$_{35}$N$_3$O$_6$S.0.4H$_2$O requires C, 49.00; H, 8.66; N, 10.08%.

EXAMPLE 5

N$^1$-Hydroxy-N$^4$-[2-hydroxy-1S-(1H-imidazol-4-ylmethyl)-ethyl]-3R-isobutyl-2S-[(methanesulfonyl-methyl-amino)-methyl]-succinamide

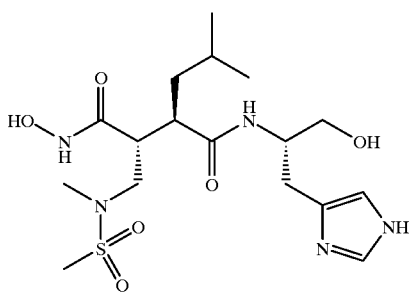

White solid. m.p. 219–221° C. $^1$H-NMR: δ((CD$_3$)$_2$SO), 11.8 (1H, br s), 10.6 (1H, s), 8.92 (1H, s), 7.87 (1H, d, J=8.3 Hz), 7.49 (1H, s), 6.77 (1H, s), 4.74 (1H, br s), 4.00 (1H, m), 3.36 (4H, br m), 2.83 (1H, m), 2.71 (3H, s), 2.59 (3H, s), 2.38 (3H,m), 1.40 (2H, m), 0.90 (1H, m), 0.81 (3H, d, J=2.2 Hz) and 0.78 (3H, d, J=2.3 Hz). $^{13}$C-NMR: δ((CD$_3$)$_2$SO), 172.7, 168.5, 134.9, 109.5, 63.5, 51.2, 50.3, 45.2, 44.8, 40.1, 39.3, 35.4, 35.0, 25.5, 24.5 and 21.7. IR: ν$_{max}$ (KBr disc), 3270, 2963, 1634, 1551, 1467, 1382, 1329, 1152 and 1109 cm$^{-1}$. Found: C, 45.48%; H, 7.23%; N, 15.46%; C$_{17}$H$_{31}$N$_5$O$_6$S.0.9H$_2$O requires C, 45.40%; H, 7.35%; N, 15.57%.

EXAMPLE 6

N$^1$-Hydroxy-N$^4$-[2-hydroxy-1S-(4-hydroxy-benzyl)-ethyl]-3R-isobutyl-2S-[(methanesulfonyl-methyl-amino)-methyl]-succinamide

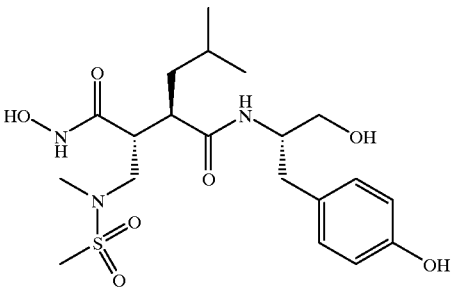

White foam. m.p. 125–128° C. $^1$H-NMR: δ(CD$_3$OD), 7.98 (1H, d, J=8.8 Hz), 7.03 (2H, d, J=8.5 Hz), 6.60 (2H, d, J=8.5 Hz), 4.14–4.07 (1H, m), 3.56–3.44 (1H, m), 3.42–3.33 (1H, m), 3.10–2.97 (1H, m), 2.85 (1H, dd, J=14.1, 4.2 Hz), 2.59 (3H, s), 2.52 (3H, s), 2.46–2.40 (1H, m), 2.33–2.26 (2H, m), 2.11–2.05 (1H, m), 1.46–1.32 (2H, m), 0.96–0.83 (1H, m), 0.78 (3H, d, J=6.8 Hz) and 0.75 (3H, d, J=6.7 Hz). 13C-NMR: δ(CD$_3$OD), 177.5, 173.3, 159.0, 133.5, 133.1, 118.4, 118.3, 67.5, 56.6, 53.7, 49.6, 48.3, 43.6, 39.2, 38.2, 38.0, 28.9, 26.6 and 23.8. IR: ν$_{max}$ (reflection disc), 3314, 2954, 1633, 1514, 1453, 1369, 1322, 1230, 1146, 1046, 968, 784 and 519 cm$^{-1}$. Found: C, 50.86%; H, 7.49%; N, 8.5%. C$_{20}$H$_{33}$N$_3$O$_7$S.0.7 H$_2$O requires: C, 50.88%; H, 7.34%; N, 8.90%.

The compounds of Examples 7–9 were prepared by analogy with Example 1, substituting the 4-methoxybenzenesulfonyl chloride for methanesulfonyl chloride in Step E:

EXAMPLE 7

N$^4$-(1S-Dimethylcarbamoyl-2,2-dimethyl-propyl)-N$^1$-hydroxy-3R-isobutyl-2S-{[(4-methoxy-benzenesulfonyl)-methyl-amino]-methyl}-succinamide

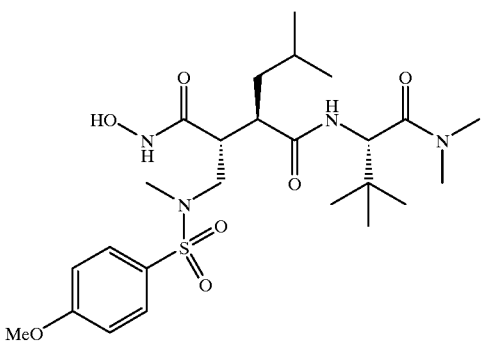

Off-white solid. m.p. 217–222° C. $^1$H-NMR: δ(CD$_3$OD), 8.03 (1H, d, J=9.1 Hz), 7.69 (2H, d, J=8.9 Hz), 7.08 (2H, d, J=8.9 Hz), 4.84 (1H, m), 3.88 (3H, s), 3.45 (1H, m), 3.16 (4H, s and m), 2.90 (4H, s and m), 2.65 (3H, s), 2.58 (1H, m), 1.53 (1H, m), 1.31 (1H, m), 1.12 (1H, m), 0.91 (9H, s), 0.85 (3H, d, J=6.5 Hz), 0.81 (3H, d, J=6.4 Hz). $^3$C-NMR: δ(CD$_3$OD), 176.3, 173.2, 171.4, 165.2, 131.3, 129.6, 116.0, 56.8, 56.7, 52.8, 47.6, 46.2, 42.0, 39.2, 37.2, 36.4, 36.3, 27.6, 27.3, 24.6 and 22.3. IR: $v_{max}$ (KBr disc) 3270, 2954, 1627, 1494, 1397, 1346, 1258, 1164, 1018 and 962 cm$^{-1}$. Found: C, 54.25%; H, 7.94%; N, 10.30%; $C_{25}H_{42}N_4O_7S$.0.6 $H_2O$ requires: C, 54.25%; H, 7.87%; N, 10.12%.

EXAMPLE 8

$N^4$-(1S-Benzyl-2-hydroxy-ethyl)-$N^1$-hydroxy-3R-isobutyl-2S-{[(4-methoxy-benzenesulfonyl)-methyl-amino]-methyl}-succinamide

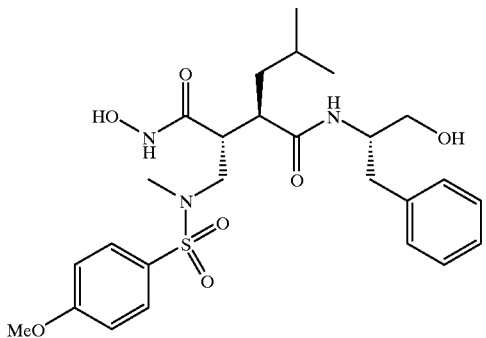

White solid. m.p. 196–203° C. $^1$H-NMR: $\delta((CD_3)_2SO)$, 10.55 (1H, d, J=1.5 Hz), 8.88 (1H, d, J=1.6 Hz), 7.92 (1H, d, J=8.1 Hz), 7.60 (2H, d, J=8.9 Hz), 7.08 (5H, m), 7.05 (2H, d, J=8.9 Hz), 4.63 (1H, m), 3.87 (1H, m), 3.71 (3H, s), 3.3 (2H, m), 2.69 (2H, m), 2.41 (6H, s and m), 2.18 (1H, m), 1.41 (2H, m), 0.94 (1H, m), 0.80 (3H, d, J=4.2 Hz) and 0.77 (3H, d, J=4.3 Hz). $^{13}$C-NMR: $\delta((CD_3)_2SO)$, 172.7, 168.3, 162.9, 139.4, 129.9, 129.2, 128.3, 128.3, 126.2, 114.7, 62.6, 55.9, 52.9, 50.7, 45.2, 44.8, 40.2, 37.0, 35.7, 25.5, 24.5 and 21.7. IR: $v_{max}$ (KBr disc), 3322, 3084, 2340, 1581, 1499, 1380, 1320, 1179, 1090, 926, 749 and 657 cm$^{-1}$. Found: C, 58.15%; H, 6.95%; N, 7.88%; $C_{26}H_{37}N_3O_7S$.0.1 $H_2O$ requires C, 58.10%; H, 6.98%; N, 7.82%.

EXAMPLE 9

3R-(3-Biphenyl4-yl-propyl)-$N^1$-hydroxy-$N^4$-[2S-hydroxy-1-(1H-imidazol-4-ylmethyly)ethyl]-2S-{[(4-methoxy-benzenesulfonyl)-methyl-amino]-methyl}-succinamide

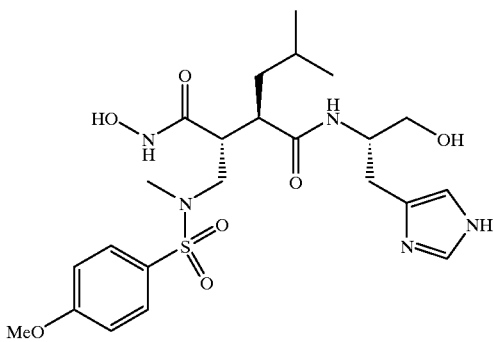

White solid. m.p. 208–209° C. $^1$H-NMR: $\delta(CD_3OD)$, 7.68 (2H, d, J=8.9 Hz), 7.39 (1H, s), 7.04 (2H, d, J=8.9 Hz), 6.77 (1H, s), 4.11 (1H, m), 3.80 (3H, s), 3.51 (2H, m), 3.21 (1 H, m), 2.80 (1H, dd, J=6.6, 15.1 Hz), 2.70–2.43 (4H, br m), 2.62 (3H, s), 1.53 (2H, m), 1.15 (1H, m), 0.88 (3H, d, J=3.3 Hz) and 0.85 (3H, d, J=3.4 Hz). $^{13}$C-NMR: $\delta(CD_3OD)$, 175.8, 171.5, 165.1, 135.8, 131.3, 129.2, 115.9, 64.5, 56.5, 53.3, 52.2, 48.7, 47.9, 46.8, 41.6, 37.3, 27.2, 24.8 and 22.1. IR: $v_{max}$ (KBr disc), 3556, 3347, 3213, 3088, 2953, 1643, 1594, 1542, 1497, 1468, 1325, 1266, 1161, 1092, 1029, 998, 954, 927, 836, 754 and 679 cm-1. Found C, 51.51%; H, 6.72%; N, 12.82%; $C_{23}H_{35}N_5O_7S$.0.6 $H_2O$ requires C, 51.50%; H, 6.80%; N, 13.06%.

The compound of Examples 10–11 were prepared by analogy with Example 1 using 3R-cyclopentylmethyl-2-methylene-succinic acid 1-benzyl ester 4-tert-butyl ester in Step C, the appropriate sulfonyl chloride in Step E and L-tert-leucinol in Step G.

EXAMPLE 10

3R-Cyclopentylmethyl-$N^1$-hydroxy-$N^4$-(1S-hydroxymethyl-2,2-dimethyl-propyl)-2S-{[(4-methoxy-benzenesulfonyl)-methyl-amino]-methyl}-succinamide

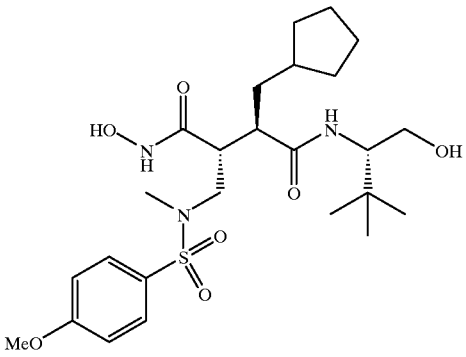

Off-white solid. m.p. 181–184° C. $^1$H-NMR: $\delta(CD_3OD)$, 7.69 (2H, d, J=8.9 Hz), 7.07 (2H, d, J=8.9 Hz), 3.88 (3H, s), 3.80–3.68 (2H, br m), 3.59–3.36 (3H, br m), 2.65 (3H, s), 2.63–2.44 (2H, br m), 1.89–1.40 (8H, br m), 1.30–1.15 (1H, m), 1.08–1.01 (2H, m), and 0.81 (9H, s). $^{13}$C-NMR: $\delta(CD_3OD)$, 176.6, 171.5, 165.7, 131.3, 129.6, 116.0, 63.0, 61.5, 56.7, 52.8, 48.4, 47.6, 47.4, 39.3, 38.6, 37.0, 35.2, 34.6, 28.2, 26.7 and 26.5. IR: $v_{max}$ (KBr disc), 3328, 2951, 1645, 1595, 1498, 1374, 1336, 1263, 1157, 1025, 940, 838, 806, 740, 660 and 563 cm$^{-1}$. Found: C, 55.36%; H, 7.89%; N, 7.49%; $C_{25}H_{41}N_3O_7S$.0.8 $H_2O$ requires C, 55.39%; H, 7.92%; N, 7.75%.

The starting material 3R-cyclopentylmethyl-2-methylene-succinic acid 1-benzyl ester 4-tert-butyl ester was prepared as follows:

Step A: 2RS-Carboxy-3R-cyclopentylmethyl-succinic acid 1-benzyl ester 4-tert-butyl ester A solution of 3R-cyclopentylmethyl-succinic acid 1-benzyl ester 4-tert-butyl ester (8.14 g, 23.5 mmol) in dry THF (140 ml) was cooled to −78° C. and treated with LDA [freshly prepared by addition of n-butyllithium to a solution of diisopropylamine (3.63 ml) in THF (140 ml) at 0° C.]. The mixture was allowed to stir for 45 minutes before transferring into a flask containing carbon dioxide pellets. After a further hour at −78° C. the reaction was allowed to warm to room temperature and quenched with saturated ammonium chloride solution. The solvents were removed under reduced pressure and the residue was extracted into ethyl acetate. The organic solution was washed successively with 1M sodium carbonate, 1M hydrochloric acid and water.

The solution was dried over anhydrous magnsium sulphate, filtered and concentrated under reduced pressure to an oil. The title compound was obtained after flash chromatography (silica gel, 5% methanol in dichloromethane). Yield 7.36 g (80%). ¹H-NMR: δ(CDCl₃), 7.33 (5H, m), 6.70 (1H, br s), 5.18 (2H, m), 3.73 (0.5H, d, J=5.3 Hz), 3.70 (0.5H, d, J=5.3 Hz), 3.01 (1H, m), 1.96–1.45 (8H, br m), 1.41 (4.5H, s), 1.40 (4.5H, s), 1.25 (1H, m) and 1.01 (2H, m).

Step B: 3R-Cyclopentylmethyl-2-methylene-succinic acid 4-tert-butyl ester

To a stirred solution of 2RS-carboxy-3R-cyclopentylmethyl-succinic acid 1-benzyl ester 4-tert-butyl ester in ethanol (200 ml) was added piperidine (2.24 m, 22.6 mmol) and 37% w/w formaldehyde solution (7.07 ml, 94.4 mmol). The mixture was stirred at room temperature for 2 days. The solvents were removed under reduced pressure and the residue was dissolved in ethyl acetate. The organic solution was washed successively with 1M hydrochloric acid and 1M sodium carbonate solution, dried over magnesium sulphate and filtered. Removal of the solvent under reduced pressure provided the desired product (6.26 g, 93%) which was used without further purification. ¹H-NMR: δ(CDCl₃), 7.37 (5H, m), 6.35 (1H, s), 5.72 (1H, s), 5.20 (2H, s), 3.45 (1H, m), 1.94–1.49 (8H, br m), 1.39 (9H, s), 1.31 (1H, m) and 1.07 (2H, m).

EXAMPLE 11

2R-Cyclopentylmethyl-3R-{[(5-dimethylamino-naphthalene-1sulfonyl)-methyl-amino]-methyl}-N⁴-hydroxy-N¹-(1S-hydroxymethyl-2,2-dimethyl-propyl)-succinamide

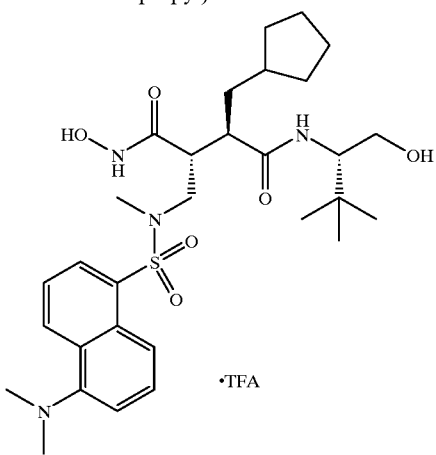

Yellow foam. m.p. 129–133° C. ¹H-NMR: δ(CD₃OD), 8.54 (1H, d, J=13.9 Hz), 8.51 (1H, d, J=14.0 Hz), 8.12 (1H, d, J=7.4 Hz), 7.66 (1H, d, J=7.6 Hz), 7.63 (1H, d, J=7.7 Hz), 7.47 (1H, d, J=7.4 Hz), 3.74–3.63 (3H, br m), 3.40 (1H, m), 3.03.(6H, s), 2.89 (1H, m), 2.78 (3H, s), 2.64 (1H, m), 2.49 (1H, m), 1.88–1.43 (8H, br m), 1.24–1.14 (1H, m), 1.08–1.04 (2H, m) and 0.71 (9H, s). ¹³C-NMR: δ(CD₃OD) 176.5 171.5, 150.4, 135.6, 132.0, 131.6, 130.9, 130.8, 129.7, 125.7, 123.3, 118.0, 63.0, 61.4, 52.3, 47.7, 46.7, 39.2, 38.6, 36.7, 35.1, 35.0, 33.0, 28.0, 26.7 and 26.4. IR: $v_{max}$ (KBr disc), 3214, 2949, 1644, 1519, 1473, 1368, 1327, 1140, 1049, 945, 836, 795, 721, 623, 584, 533 and 461 cm⁻¹. Found C, 54.40%; H, 7.00%; N, 8.02%; C₃₂H₄₇N₄O SF₃.0.1 H₂O requires C, 54.39%; H, 6.73%; N, 7.93%.

The compound of Examples 12–14 were prepared by analogy with Example 1 using 3R-(3-biphenyl-4-yl-propyl)-2-methylene-succinic acid 1-benzyl ester 4-tert-butyl ester in Step C, the appropriate sulfonyl chloride in Step E and L-phenylalaninol or L-tert-leucinol in Step G.

EXAMPLE 12

N⁴-(1S-Benzyl-2-hydroxy-ethyl)-3R-(3-biphenyl-4-yl-propyl)-N¹-hydroxy-2S-[(methanesulfonyl-methyl-amino)-methyl]-succinamide

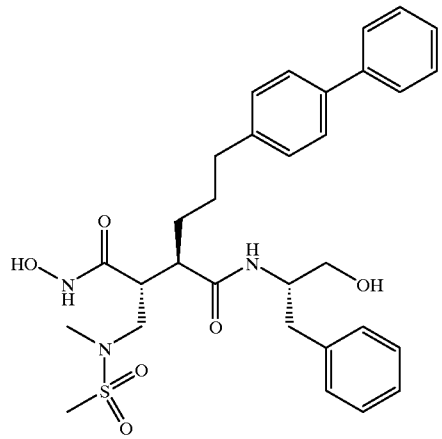

White solid. m.p. 201–207° C. ¹H-NMR: δ(CD₃OD), 8.16 (1H, d, J=8.9 Hz), 7.60–7.12 (14H, m), 4.33–4.19 (1H, m), 3.54–3.47 (2H, m), 3.29–3.18 (1H, m), 3.03 (1H, dd, J=4.4, 13.9 Hz), 2.70 (3H, s), 2.58 (3H, s), 2.73–2.50 (3H, m), 2.57–2.28 (2H, m), 2.13–2.02 (1H, m) and 1.70–1.33 (4H, m). ¹³C-NMR: δ(CD₃OD), 175.5, 171.5, 142.9, 140.6, 140.4, 130.8, 130.3, 130.2, 129.9, 128.4, 128.3, 128.2, 128.0, 65.7, 54.7, 51.8, 48.1, 47.1, 38.4, 37.5, 36.6, 35.7, 32.1 and 30.3. IR: $v_{max}$ (reflection disc), 3299, 2943, 1636, 1537, 1323, 1136, 975 cm⁻¹.

The starting material was prepared from 3R-(3-biphenyl-4-yl-propyl)-succinic acid 1-benzyl ester 4-tert-butyl ester by analogy with 3R-cyclopentylmethyl-2-methylene-succinic acid 1-benzyl ester 4-tert-butyl ester (see Example 10).

EXAMPLE 13

3R-(3-Biphenyl4-yl-propyl)-N¹-hydroxy-N⁴-(1S-hydroxymethyl-2,2-dimethyl-propyl)-2S-{[(4-methoxy-benzenesulfonyl)-methyl-amino]-methyl}-succinamide

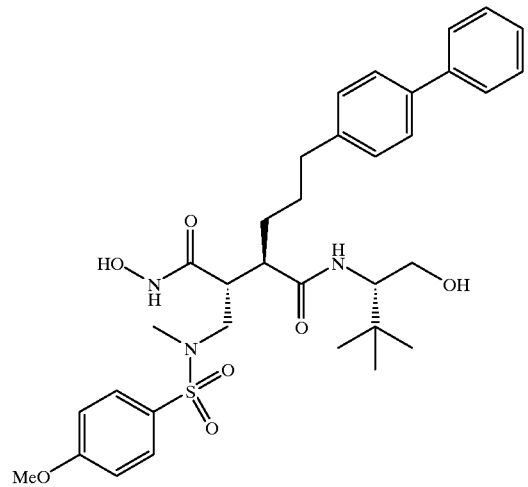

White solid. m.p. 226–228° C. ¹H-NMR: δ((CD₃)₂SO), 10.63 (1H, s), 8.96 (1H, s), 7.66–7.29 (9H, m), 7.25 (2H, d, J=8.0 Hz), 7.10 (2H, d, J=8.8 Hz), 4.35–4.24 (1H, t, J=4.3 Hz), 3.84 (3H, s), 3.62–3.42 (3H, m), 3.32–3.15 (1H, m), 2.52 (3H, s), 2.70–2.48 (4H, m), 2.30–2.20 (1H, m), 1.80–1.60 (1H, m), 1.56–1.23 (3H, m) and 0.72 (9H, s). $^3$C-NMR: $\delta((CD_3)_2SO)$, 173.3, 168.4, 162.9, 141.8, 140.6, 137.8, 129.8, 129.2, 127.7, 127.4, 126.8, 114.9, 61.4, 59.1, 56.1, 51.1, 46.5, 44.2, 35.6, 35.2, 33.6, 31.0, 28.1 and 27.4. IR: $\nu_{max}$ (reflection disc), 3238, 2845, 1643, 1534, 1343 cm$^{-1}$. Found: C, 63.79%; H, 6.98%; N, 6.48%; S, 5.20%. $C_{34}H_{45}N_3O_7S$ requires: C, 63.83%; H, 7.09%; N, 6.57%; S 5.01%.

EXAMPLE 14

N$^4$-(1S-Benzyl-2-hydroxy-ethyl)-3R-(3-biphenyl-4-yl-propyl)-N$^1$-hydroxy-2S-{[(4-methoxy-benzenesulfonyl)-methyl-amino]-methyl}-succinamide

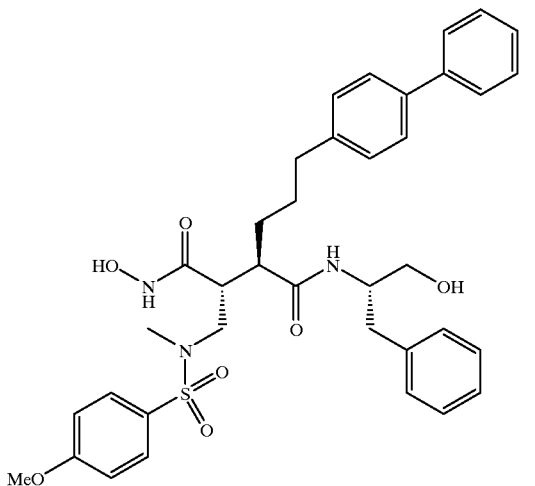

White solid. m.p. 245–247° C. $^1$H-NMR: $\delta((CD_3)_2SO)$, 10.61 (1H, s), 8.91 (1H, s), 7.96 (1H, d, J=8.2 Hz), 7.79–6.98 (18H, m), 4.69 (1H, t, J=5.2 Hz), 3.99–3.82 (1H, m), 3.72 (3H, s), 3.40–3.16 (3H, m), 2.74 (1H, dd, J=6.2, 13.7 Hz), 2.68–2.28 (5H, m), 2.43 (3H, s), 2.21–2.09 (1H, m) and 1.61–1.23 (4H, m). $^{13}$C-NMR: $\delta((CD_3)_2SO)$, 172.6, 168.3, 162.9, 141.8, 140.5, 139.4, 137.9, 129.9, 129.2, 129.2, 128.3, 128.2, 127.5, 126.9, 126.8, 126.2, 114.8, 62.8, 55.9, 52.9, 50.7, 46.4, 44.8, 37.0, 35.8, 35.1, 30.7 and 28.7. IR: $\nu_{max}$ (reflection disc), 3306, 2942, 1641, 1535, 1455 and 1330 cm$^{-1}$. C, 65.42%; H, 6.43%; N, 6.12%; S, 4.92%. $C_{37}H_{43}N_3O_7S.0.3\,H_2O$ requires: C, 65.43%; H, 6.47%; N, 6.19%.

What is claimed is:

1. A compound of formula (I)

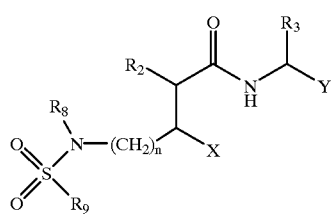

wherein

X is —COOH or —CONHOH n is 1, 2, 3 or 4;

$R_2$ is a heteroaryl($C_1$–$C_6$ alkyl)-, non-aryl heterocyclyl($C_1$–$C_6$ alkyl)-, heteroaryloxy($C_1$–$C_6$ alkyl)-, phenyl($C_1$–$C_6$ alkyl)O($C_1$–$C_6$ alkyl)-, heteroaryl($C_1$–$C_6$ alkyl)O($C_1$–$C_6$ alkyl)-, or heteroaryl($C_1$–$C_6$ alkyl)S($C_1$–$C_6$ alkyl)- group, any one of which may be optionally substituted by $C_1$–$C_6$ alkyl, trifluoromethyl, $C_1$–$C_6$ alkoxy, halo, cyano (—CN), phenyl, substituted phenyl or heteroaryl; or $R_3$ represents (a) the characterising group of a natural or non-natural α amino acid in which any functional groups may be protected, provided that $R_3$ does not comprise a heterocyclic or heteroaryl group; or (b) a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl;

$R_8$ is hydrogen, $C_1$–$C_6$ alkyl, benzyl, acyl, optionally substituted phenyl, an amino protecting group, or a group —(CH$_2$)$_m$COZ where m is an integer from 1 to 6, and Z represents OH, $C_1$–$C_6$ alkoxy or —NR$_x$R$_y$ where R$_x$, R$_y$ each independently represent hydrogen or $C_1$–$C_6$ alkyl; and; and $R_9$ is optionally substituted $C_1$–$C_6$ alkyl, cycloalkyl, cycloalkenyl, di-($C_1$–$C_6$ alkyl)amino, heterocyclyl, phenyl, naphthyl, or heteroaryl; or $R_8$ and $R_9$ taken together represent a divalent $C_3$–$C_6$ alkylene or alkenylene group which may optionally be (i) substituted by an oxo group, and/or (ii) substituted by ($C_1$–$C_6$)alkoxy, hydroxy, mercapto, ($C_1$–$C_6$) alkylthio, amino, halo (including fluoro, chloro, bromo and iodo), cyano, trifluoromethyl, nitro, —COOH, —CONH$_2$, —CONHR$^A$ or —CONR$^A$R$^A$ wherein R$_A$ is a ($C_1$–$C_6$)alkyl group, and/or (iii) fused to a phenyl or heteroaryl group which itself may be substituted;

Y is a group of formula (ID) or (IE)

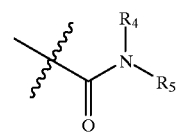

(ID)

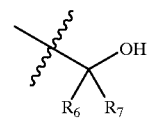

(IE)

wherein:

$R_4$ represents (a) an optionally substituted cycloalkyl or cycloalkenyl ring; or (b) a phenyl or heteroaryl ring which may be fused to a benzene or heteroaryl ring, either or both of which rings may be substituted, and in which any ring nitrogen atom may be oxidised as an N-oxide, or (c) a group —CHR$^x$R$^y$ wherein R$^x$ and R$^y$ each independently represents an optionally substituted phenyl or heteroaryl ring which may be linked covalently to each other by a bond or by a $C_1$–$C_4$ alkylene or $C_2$–$C_4$ alkenylene bridge;

(d) a group of formula —(Z'—O)$_w$—Z wherein Z' is straight or branched $C_1$–$C_6$ alkyl optionally interrupted by one or more non-adjacent S and/or N atoms, w is an integer >1, and no continuous linear sequence of atoms in the group $R_4$ is >12, or (e) a straight or branched $C_1$–$C_6$ alkyl group, optionally interrupted by one or more non-adjacent S and/or N atoms, which is substituted by at least two substituents of formula —(Z''')$_x$—(OZ)$_q$ wherein Z''' is straight or branched $C_1$–$C_6$ alkyl optionally interrupted by one or more non-adjacent S and/or N atoms, x is 0 or 1, q is 1 or 2, and no continuous linear sequence of atoms in the group $R_4$ is >12, or (f) hydrogen, $C_1$–$C_6$ alkyl, $C_1$–$C_4$ perfluoroalkyl, or a group D-$C_1$–$C_6$ alkyl)- wherein D is hydroxy, $C_1$–$C_6$ alkoxy, $C_1$–$C_6$ alkylthio, acylamino, optionally substituted phenyl or heteroaryl, $NH_2$, or mono- or di-($C_1$–$C_6$ alkyl)amino or N-morpholino;

or $R_3$ and $R_4$ taken together represent a divalent chain of formula —C($R^a$)($R^b$)—A''-Alk- wherein $R^a$ and $R^b$ are independently hydrogen or $C_1$–$C_6$ alkyl, A'' is a bond, —O—, —S—, —S—S—, —NH— or —NR$^a$— wherein $R^a$ is $C_1$–$C_6$ alkyl, and Alk is $C_1$–$C_6$ alkylene;

$R_5$ is hydrogen or a $C_1$–$C_6$ alkyl group;

$R_6$ is hydrogen, $C_1$–$C_6$ alkyl, phenyl($C_1$–$C_6$ alkyl), heterocyclyl($C_1$–$C_6$ alkyl), optionally substituted phenyl, or optionally substituted heterocyclyl;

$R_7$ is hydrogen or a $C_1$–$C_6$ alkyl group;

or (when $R_7$ is hydrogen) $R_3$ and $R_7$ taken together with the carbon atoms to which they are attached form a 2-hydroxycyclohexyl or $C_6$ sugar (hexose) ring;

or $R_6$ and $R_7$ taken together with the carbon atom to which they are attached form a 5 or 6-membered carbocyclic or heterocyclic ring;

or a pharmaceutically acceptable salt, hydrate or solvate thereof.

2. A compound as claimed in claim 1 wherein the stereochemistry is as follows:

C atom carrying the X group —S,
C atom carrying the $R_2$ group —R,
C atom carrying the $R_3$ group —S.

3. A compound as claimed in claim 1 wherein $R_2$ is a radical of formula (A) or (B):

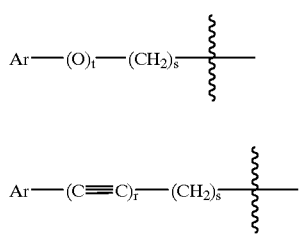

wherein
Ar represents an optionally substituted heteroaryl group;
r is 1 or 2;
s is 0, 1, 2, 3 or 4; and
t is 0 or 1.

4. A compound as claimed in claim 1 wherein $R_2$ is 4'-pyrid-2,3 or 4-yl(phenyl($C_1$–$C_6$ alkyl))- or 4'-pyrid-2,3 or 4-yloxy(phenyl($C_1$–$C_6$ alkyl))-, either of which may optionally be substituted in the terminal pyridyl ring by halogen, cyano, $C_1$–$C_6$ alkyl, or $C_1$–$C_6$ alkoxy.

5. A compound as claimed in claim 1 wherein $R_2$ is 4-pyrid-4-yloxyphenylethyl or 4-(4-chlorophenoxy) phenylethyl.

6. A compound as claimed claim 1 wherein $R_3$ is $C_1$–$C_6$ alkyl, benzyl, 2,- 3-, or 4-hydroxybenzyl, 2,- 3-, or 4-benzyloxybenzyl, 2,- 3-, or 4-$C_1$–$C_6$ alkoxybenzyl, or benzyloxy($C_1$–$C_6$alkyl)-.

7. A compound as claimed in claim 1 wherein $R_3$ is the characterising group of a natural α amino acid, in which any functional group may be protected, any amino group may be acylated and any carboxyl group present may be amidated.

8. A compound as claimed claim 1 wherein $R_3$ is a group —(Alk)$_n$$R_{10}$ where Alk is a ($C_1$–$C_6$)alkyl or ($C_2$–$C_6$)alkenyl group optionally interrupted by one or more —O—, or —S— atoms or —N($R_{11}$)— groups, where $R_{11}$ is a hydrogen atom or a ($C_1$–$C_6$)alkyl group, n is 0 or 1, and $R_{10}$ is an optionally substituted cycloalkyl or cycloalkenyl group; or a benzyl group substituted in the phenyl ring by a group of formula —OCH$_2$COR$_{12}$ where $R_{12}$ is hydroxyl, amino, ($C_1$–$C_6$)alkoxy, phenyl($C_1$–$C_6$)alkoxy, ($C_1$–$C_6$)alkylamino, di(($C_1$–$C_6$)alkyl)amino, phenyl($C_1$–$C_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid.

9. A compound as claimed in claim 1 wherein $R_3$ is a group —C$R_a$$R_b$$R_c$ in which:

each of $R_a$, $R_b$ and $R_c$ is independently hydrogen, ($C_1$–$C_6$) alkyl, ($C_2$–$C_6$)alkenyl, ($C_2$–$C_6$)alkynyl, phenyl($C_1$–$C_6$) alkyl, ($C_3$–$C_8$)cycloalkyl; or $R_c$ is hydrogen, ($C_1$–$C_6$)alkyl, ($C_2$–$C_6$)alkenyl, ($C_2$–$C_6$) alkynyl, phenyl($C_1$–$C_6$)alkyl, or ($C_3$–$C_8$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring; or $R_a$ and $R_b$ are each independently ($C_1$–$C_6$)alkyl, ($C_2$–$C_6$) alkenyl, ($C_2$–$C_6$)alkynyl, phenyl($C_1$–$C_6$)alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_1$–$C_4$)perfluoroalkyl, —CH$_2$OH, —CO$_2$ ($C_1$–$C_6$)alkyl, —O($C_2$–$C_6$)alkyl, —O($C_2$–$C_6$)alkenyl, —S($C_1$–$C_6$)alkyl, —SO($C_1$–$C_6$)alkyl, —SO$_2$($C_1$–$C_6$) alkyl, —S($C_2$–$C_6$)alkenyl, —SO($C_2$–$C_6$)alkenyl, —SO$_2$($C_2$–$C_6$)alkenyl or a group —Q—W wherein Q represents a bond or —O—, —S—, —SO— or —SO$_2$— and W represents a phenyl, phenylalkyl, ($C_3$–$C_8$)cycloalkyl, ($C_3$–$C_8$)cycloalkylalkyl, ($C_4$–$C_8$) cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$–$C_6$)alkyl, —CONH$_2$, —CONH ($C_1$–$C_6$)alkyl, —CONH($C_1$–$C_6$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$($C_1$–$C_6$) alkyl, —NO$_2$, —NH$_2$, —NH($C_1$–$C_6$)alkyl, —N(($C_1$–$C_6$)alkyl)$_2$, —NHCO($C_1$–$C_6$)alkyl, ($C_1$–$C_6$)

alkyl, $(C_2–C_6)$alkenyl, $(C_2–C_6)$alkynyl, $(C_3–C_8)$ cycloalkyl, $(C_4–C_8)$cycloalkenyl, phenyl or benzyl.

10. A compound as claimed in claim 1 wherein $R_3$ is iso-butyl, 1-fluoro-1-methylethyl, 1-hydroxy-1-methylethyl, 1-methoxy-1-methylethyl, 1-benzylthio-1-methylethyl, or 1-methylthio-1-methylethyl.

11. A compound as claimed in claim 1 wherein $R_3$ is benzyl, t-butyl, 1-mercapto-1-methylethyl or 3H-imidazol-4-yl-methyl.

12. A compound as claimed in claim 1 wherein Y is a group (ID) and $R_4$ is cyclopropyl, cyclobutyl, cyclopentyl, cyclohexyl cycloheptyl or cyclooctyl; phenyl, 2-methoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulphonylphenyl, 3-methylsulphonylphenyl, 4-methylsulphonylphenyl, 2-trifluoromethylphenyl, 3-trifluoromethylphenyl, 4-trifluoromethylphenyl, 3,5-ditrifluoro-methylphenyl, 2-aminophenyl, 3-aminophenyl, 4-aminophenyl, 2-N,N-dimethyl-aminophenyl, 3-N,N-dimethylaminophenyl, 4-N,N-dimethylaminophenyl, 2-hydroxyphenyl, 3-hydroxyphenyl, 4-hydroxyphenyl, 2-napthyl, furan-2-yl, thien-2-yl, pyrrol-2-yl, tetrahydrofuran-2-yl, imidazol-2-yl, thiazol-2-yl, 4-ethoxycarbonyl-methylthiazol-2-yl, 4-phenylthiazol-2-yl, 4,5-dimethylthiazol-2-yl, 5-bromothiazol-2-yl, 4-tert-butylthiazol-2-yl, benzothiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1,2,4-thiadiazol-5-yl, 1,3,4-thiadiazol-2-yl, 5-methyl-1,3,4-thiadiazol-2-yl, pyridin-2-yl, pyridin-3-yl, pyridin-4-yl, N-oxides of pyridin-2-yl pyridin-3-yl and pyridin-4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo[b]thien-2-yl, isoxazol-5-yl, or quinolin-3-yl, a group —$CHR^xR^y$ wherein $R^x$ and $R^y$ independently represent optionally substituted phenyl, thienyl, furyl, pyrrolyl, imidazolyl, thiazolyl, pyrazolyl, isoxazolyl, isothiazolyl, triazolyl, thiadiazolyl, oxadiazolyl, pyridinyl, pyridazinolyl, pyrimidinyl, piperazinyl or triazinyl, a polyether chain possessing at least two non-adjacent oxygen atoms, for example 2-(2-methoxyethoxymethoxy)ethyl, 1,1-dimethyl-2-(2-methoxyethoxymethoxy)ethyl, 2-(2-ethoxyethoxymethoxy)ethyl, 2-(2-(2-methoxyethoxy)ethoxy)ethyl, 2-(2-(3-methoxypropoxymethoxy)ethyl, 3-(2-methoxyethoxymethoxy)propyl, 2,2-dimethyl-3-(2-methoxyethoxymethoxy)propyl, 2-(2-methoxyethoxy)ethyl, 3-(2-methoxyethoxy)-propyl, 2-methyl-2,2-di(2-methoxyethyl)propyl, 2-methyl-2,2-di(2-methoxyethyl)butyl, or 2-methyl-2,2-di(2-methoxymethyl)propyl;

methyl, ethyl, n- or iso-propyl, n-, sec- or tert-butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone)propyl, morpholin-4-ylpropyl, optionally substituted phenylethyl, phenylpropyl, phenylbutyl, or phenylpentyl.

13. A compound as claimed in claim 1 wherein Y is a group (ID) and $R_4$ is 3-methoxyphenyl, pyridin-2-yl, pyridin-3-yl, pyridin-4-yl, thiazol-2-yl, 4-ethoxycarbonylmethylthiazol-2-yl, 5-methyl-1,3,4-thiadiazol-2-yl, 4-tert-butylthiazol-2-yl, 2-(2-methoxyethoxy)ethyl, methyl or morpholin-4-ylpropyl.

14. A compound as claimed in claim 1 wherein Y is a group (ID) and $R_3$ and $R_4$ taken together represent a divalent chain of formula —$C(R^a)(R^b)$—A—Alk— wherein $R^a$ and $R^b$ are independently hydrogen or $C_1$–$C_6$ alkyl, A is a bond, —O—, —S—, —S—S—, —NH— or —$NR^a$— wherein $R^a$ is $C_1$–$C_6$ alkyl, and Alk is $C_1$–$C_6$ alkylene.

15. A compound as claimed claim 1 wherein Y is a group (ID) and $R_3$ and $R_4$ taken together represent —$C(CH_3)_2$ $SCH_2CH_2CH_2$—, or —$C(CH_3)_2SSCH_2CH_2$—.

16. A compound as claimed in claim 1 wherein Y is a group (ID) and $R_5$ is hydrogen or ethyl.

17. A compound as claimed in claim 1 wherein Y is a group (ID) and $R_5$ is methyl.

18. A compound as claimed in claim 1 wherein Y is a group (ID) and $R_4$ and $R_5$ are both methyl.

19. A compound as claimed in claim 1 wherein Y is a group (IE) and $R_6$ is hydrogen, methyl, ethyl, benzyl or pyridylmethyl.

20. A compound as claimed claim 1 wherein Y is a group (IE) and $R_7$ is hydrogen or methyl.

21. A compound as claimed in claim 1 wherein Y is a group (IE) and $R_6$ and $R_7$ taken together with the carbon atom to which they are attached form, for a cyclopentyl, cyclohexyl or morpholino ring.

22. A compound as claimed in claim 1 wherein Y is a group (IE) and $R_6$ and $R_7$ are both hydrogen.

23. A compound as claimed in claim 1 wherein Y is a group (IE), $R_7$ is hydrogen, and $R_3$ and $R_6$ taken together with the carbon atoms to which they are attached form a 2-hydroxycyclohexyl or a glucose ring.

24. A compound as claimed in claim 1 wherein $R_8$ is ethyl, n- or iso-propyl, n-, sec- or tert-butyl, n-pentyl, n-hexyl, or benzyl.

25. A compound as claimed in claim 1 wherein $R_6$ is hydrogen, acetyl or methyl.

26. A compound as claimed in claim 1 wherein $R_9$ is substituted or unsubstituted methyl, ethyl, n- or iso-propyl, n-, sec- or tert-butyl, n-pentyl, n-hexyl, cyclopropyl, cyclobutyl, cyclopentyl, cyclohexyl, cycloheptyl, cyclooctyl, cyclopentenyl, cyclohexenyl, cycloheptenyl, cyclooctenyl, dimethyl- or diethyl-amino, phenyl, naphthyl, thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl or triazinyl.

27. A compound as claimed in claim 1 wherein $R_9$ is benzyl, 2-methoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulfonylphenyl, 3-methylsulfonylphenyl, 4-methylsulfonylphenyl, 2-trifluoromethylphenyl, 3-trifluoromethylphenyl, 4-trifluoromethylphenyl, 3,5-ditrifluoromethylphenyl, 2-aminophenyl, 3-aminophenyl, 4-aminophenyl, 2-N,N-dimethylaminophenyl, 3-N,N-dimethylaminophenyl, 4-N,N-dimethylaminophenyl, 2-hydroxyphenyl, 3-hydroxyphenyl, 4-hydroxyphenyl, naphth-1-yl and naphth-2-yl; furan-2-yl, thien-2-yl, imidazol-2-yl, thiazol-2-yl, 4-ethoxycarbonylmethyl-thiazol-2-yl, 4-phenylthiazol-2-yl, 4,5-dimethylthiazol-2-yl, 5-bromothiazol-2-yl, 4-tert-butylthiazol-2-yl, benzothiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1,2,4-thiadiazol-5-yl, 1,3,4-thiadiazol-2-yl, 5-methyl-1,3,4-thiadiazol-2-yl, pyridin-2-yl, pyridin-3-yl, pyridin-4-yl, N-oxides of pyridin-2-yl, pyridin-3-yl and pyridin-4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo(b)thien-2-yl, isoxazol-5-yl, and quinolin-3-yl.

28. A compound as claimed in claim 1 wherein $R_9$ is methyl, dimethylamino, trifluoromethyl, phenyl, 4-methoxyphenyl, 4-chlorophenyl, naphth-1-yl, naphth-2-yl or thien-2-yl.

29. A compound as claimed in claim 1 wherein $R_8$ and $R_9$ taken together with the N and S atoms to which they are attached represent a group of formula (XI) or (XII)

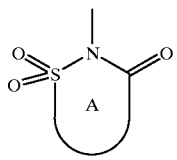

(XI)

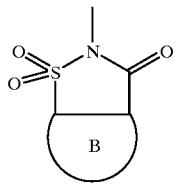

(XII)

wherein ring A is a substituted or unsubstituted, saturated or unsaturated 5–8 membered ring and ring B is a substituted or unsubstituted fused phenyl or heteroaryl (e.g. thienyl or pyridinyl) ring.

30. A compound as claimed in claim 1 selected from the group consisting of $N^1$-hydroxy-$N^4$-(2-hydroxy-1S-(1H-imidazol-4-ylmethyl)-ethyl)-3R-isobutyl-2S-((methanesulfonyl-methyl-amino)-methyl)-succinamide, 3R-(3-biphenyl-4-yl-propyl)-$N^1$-hydroxy-$N^4$-(2S-hydroxy-1-(1H-imidazol-4-ylmethyl)-et hyl)-2S-{((4-methoxy-benzenesulfonyl)-methyl-amino)-methyl}-succinamide, and pharmaceutically acceptable salts, hydrates and solvates thereof.

31. A pharmaceutical composition comprising a compound as claimed in claim 1, together with a pharmaceutically acceptable carrier.

32. A composition as claimed in claim 31 adapted for oral administration.

* * * * *